(12) United States Patent
Dalie et al.

(10) Patent No.: US 7,135,555 B2
(45) Date of Patent: Nov. 14, 2006

(54) MAMMALIAN TNF-α CONVERTASES

(75) Inventors: Barbara Dalie, Annandale, NJ (US); Xuedong Fan, Union, NJ (US); Daniel Lundell, Flemington, NJ (US); Charles A. Lunn, Somerville, NJ (US); Jimmy C. Tan, Edison, NJ (US); Paul J. Zavodny, Mountainside, NJ (US)

(73) Assignee: Schering Corporation, Kenilworth, NJ (US)

( * ) Notice: Subject to any disclaimer, the term of this patent is extended or adjusted under 35 U.S.C. 154(b) by 346 days.

(21) Appl. No.: 10/145,014

(22) Filed: May 14, 2002

(65) Prior Publication Data

US 2002/0168755 A1 Nov. 14, 2002

Related U.S. Application Data

(60) Continuation of application No. 09/982,308, filed on Oct. 17, 2001, now Pat. No. 6,531,290, which is a division of application No. 09/156,163, filed on Sep. 17, 1998, now Pat. No. 6,319,681, which is a division of application No. 08/889,909, filed on Jul. 10, 1997, now Pat. No. 5,853,977.

(60) Provisional application No. 60/021,710, filed on Jul. 12, 1996.

(51) Int. Cl.
*C07K 16/00* (2006.01)
*A61K 39/395* (2006.01)
*G01N 33/53* (2006.01)
*C12P 21/04* (2006.01)

(52) U.S. Cl. .............................. 530/387.9; 530/388.26; 530/388.1; 530/391.1; 530/391.7; 424/139.1; 424/141.1; 424/146.1; 424/178.1; 435/70.21

(58) Field of Classification Search .............. 530/387.1, 530/387.3, 387.9, 388.1, 388.26, 391.1, 391.7, 530/389.1; 424/130.1, 133.1, 139.1, 141.1, 424/146.1, 178.1, 70.21

See application file for complete search history.

(56) References Cited

U.S. PATENT DOCUMENTS

| | | | |
|---|---|---|---|
| 5,270,202 A * | 12/1993 | Raychaudhuri | |
| 5,594,106 A | 1/1997 | Black et al. | |
| 5,629,285 A | 5/1997 | Black et al. | |
| 5,753,653 A | 5/1998 | Bender et al. | |
| 5,858,705 A * | 1/1999 | Wei et al. | |
| 6,235,280 B1 * | 5/2001 | Chatterjee et al. | |
| 6,632,431 B1 * | 10/2003 | Wu | |
| 2003/0027260 A1 * | 2/2003 | Goddard et al. | |

FOREIGN PATENT DOCUMENTS

| | | |
|---|---|---|
| WO | WO 91/02540 | 3/1991 |
| WO | WO 95/24501 | 9/1995 |
| WO | WO 96/41624 | 12/1996 |

OTHER PUBLICATIONS

Rudikoff et al. Proc. Natl. Acad. Sci. USA , vol. 79:1979-1983, 1982.*
Coleman P. M. Research in Immunology, 145:33-36, 1994.*
Caspar et al. Blood, 90(9):3699-3706, 1997.*
Lien et al. The Journal of Biological Chemistry, 274(47):33419-33425, Nov. 19, 1999.*
Yang et al. Nature, 395:284-288, 1998.*
Black et al., "Identification of a TNF Converting Enzyme and its Validation as a Target for Drug Development", *FASEB J.*, vol. 9, No. 4, p. A1254 (1995).
Black et al., "Relaxed Specificity of Matrix Metalloproteinases (MMPS) and TIMP Insensitivity of Tumor Necrosis Factor-α (TNF-α) Production Suggest the Major TNF-α Converting Enzme Is Not an MMP", *Biochem. and Biophys. Res. Comm.*, vol. 225, pp. 400-405 (1996).
Black et al., "A metalloproteinase disintegrin that releases tumour-necrosis factor-α from cells", *Nature*, vol. 385, pp. 729-733 (1997).
Black et al., Cloning of a Membrane-Bound TNFα Converting Enzyme (TACE), *European Cytokine Network*, vol. 7, No. 2, ISSN: 1148-5493 (1996).
Freije et al., "Molecular Cloning and Expression of Collagenase-3, a Novel Human Matrix Metalloproteinase Produced by Breast Carcinomas", *J. Biol. Chem.*, vol. 269, pp. 16766-16773 (1994).
Gearing et al., "Processing of tumour necrosis factor-α precursor by metalloproteinases", *Nature*, vol. 370, pp. 555-557 (1994).
Hillier et al., EMBL/GENBANK/DDBJ Databases, Accession No.; T9345: Identification No. HS48563.
Howard et al., "Molecular cloning of MADM: a catalytically active mammalian disintegrin-metalloprotease expressed in various cell types", *Biochem. J.*, vol. 317, pp. 45-50 (1996).
Lunn et al., "Purification of ADAM 10 from bovine spleen as a TNFα convertase", *FEBS Letters*, vol. 400, pp. 333-335 (1997).

(Continued)

*Primary Examiner*—Larry R. Helms
*Assistant Examiner*—David J. Blanchard
(74) *Attorney, Agent, or Firm*—Michael G. Biro; Melodie W. Henderson; Grant E. Reed

(57) ABSTRACT

The present invention provides isolated human and bovine TNF-α convertases, nucleic acids and recombinant vectors encoding the same, host cells comprising the nucleic acids and vectors, and methods for making the convertases using the host cells. This invention further provides antibodies and antigen binding fragments thereof which specifically bind to the convertases and are useful for treating medical conditions caused or mediated by TNF-α. Also provided are screening methods for identifying specific inhibitors of mammalian TNF-α convertases, and for identifying nucleic acids encoding such convertases.

10 Claims, 3 Drawing Sheets

OTHER PUBLICATIONS

McGeehan et al., "Regulation of tumour necrosis factor-α processing by a metalloproteinase inhibitor", *Nature*, vol. 370, pp. 558-561 (1994).

Mohler et al., "Protection against a lethal dose of endotoxin by an inhibitor of tumour necrosis factor processing", *Nature*, vol. 370, pp. 218-220 (1994).

Okada et al., "Membrane-type matrix metalloproteinase (MT-MMP) gene is expressed in stromal cells of human colon, breast, and head and neck carcinomas", *Proc. Nat. Acad. Sci.*, vol. 92, pp. 2730-2734 (1995).

Puente et al., "Molecular Cloning of a Novel Membrane-type Matrix Metalloproteinase from a Human Breast Carcinoma", *Cancer Res.*, vol. 56, pp. 944-949 (1996).

Robache-Gallea et al., "*In Vitro* Processing of Human Tumor Necrosis Factor-α", *J. Biol. Chem.*, vol. 270, pp. 23688-23692 (1995).

Sato et al., "A matrix metalloproteinase expressed on the surface of invasive tumour cells", *Nature*, vol. 370, pp. 61-65 (1994).

Takino et al., "Identification of the Second Membrane-type Matrix Metalloproteinase (MT-MMP-2) Gene from a Human Placenta cDNA Library", *J. Biol. Chem.*, vol. 270, pp. 23013-23020 (1995).

Will et al., "cDNA sequence and mRNA tissue distribution of a novel human matrix metalloproteinase with a potential transmembrane segment", *Eur. J. Biochem.*, vol. 231, pp. 602-608 (1995).

Woessner, Jr., "Matrix metalloproteinases and their inhibitors in connective tissue remodeling", *FASEB. J.*, vol. 5, vol. 2145-2154 (1991).

Wolfsberg et al., "ADAM, a Novel Family of Membrane Proteins Containing A Disintegrin And Metalloprotease Domain: Multipotential Functions in Cell-Cell and Cell-Matrix Interactions", *J. Cell Biology*, vol. 131, pp. 275-278 (1995).

Kim et al., "Pro-tumour necrosis factor cleavage enzyme in macrophage membrane/particulate", *Immunology*, vol. 80, pp. 134-139 (1993).

* cited by examiner

SEQUENCE LISTING

<160> NUMBER OF SEQ ID NOS: 23

<210> SEQ ID NO 1
<211> LENGTH: 699
<212> TYPE: DNA
<213> ORGANISM: Homo sapiens

<400> SEQUENCE: 1

```
atgagcactg aaagcatgat ccgggacgtg gagctggccg aggaggcgct ccccaagaag      60
acaggggggc cccagggctc caggcggtgc ttgttcctca gcctcttctc cttcctgatc     120
gtggcaggcg ccaccacgct cttctgcctg ctgcactttg gagtgatcgg ccccagagg     180 gaagagttcc ccagggacct ctctctaatc agccctctgg cccaggcagt cagatcatct     240
tctcgaaccc cgagtgacaa gcctgtagcc catgttgtag caaaccctca agctgagggg     300
cagctccagt ggctgaaccg ccgggccaat gccctcctgg ccaatggcgt ggagctgaga     360
gataaccagc tggtggtgcc atcagagggc ctgtacctca tctactccca ggtcctcttc     420
aagggccaag gctgcccctc cacccatgtg ctcctcaccc acaccatcag ccgcatcgcc     480
gtctcctacc agaccaaggt caacctcctc tctgccatca gagcccctg ccagagggag     540 accccagagg gggctgaggc caagccctgg tatgagccca tctatctggg aggggtcttc     600
cagctggaga agggtgaccg actcagcgct gagatcaatc ggcccgacta tctcgacttt     660
gccgagtctg ggcaggtcta ctttgggatc attgccctg                             699
```

```
<210> SEQ ID NO 2
<211> LENGTH: 9
<212> TYPE: PRT
<213> ORGANISM: Bovine spleen
<220> FEATURE:
<221> NAME/KEY: MISC_FEATURE
<222> LOCATION: (6)..(6)
<223> OTHER INFORMATION: X may be either G or D

<400> SEQUENCE: 2

Met Asn Ser Leu Leu Xaa Ser Ala Pro
1               5

<210> SEQ ID NO 3
<211> LENGTH: 193
<212> TYPE: PRT
<213> ORGANISM: Artificial Sequence
<220> FEATURE:
<223> OTHER INFORMATION: protein substrate of TNF-alpha convertase

<400> SEQUENCE: 3

Met Asp Tyr Lys Asp Asp Asp Lys Gly Ser His Phe Gly Val Ile
1               5                   10                  15

Gly Pro Gln Arg Glu Glu Ser Pro Arg Asp Leu Ser Leu Ile Ser Pro
                20                  25                  30

Leu Ala Gln Ala Val Arg Ser Ser Ser Arg Thr Pro Ser Asp Lys Pro
            35                  40                  45

Val Ala His Val Val Ala Asn Pro Gln Ala Glu Gly Gln Leu Gln Trp
        50                  55                  60

Leu Asn Arg Arg Ala Asn Ala Leu Leu Ala Asn Gly Val Glu Leu Arg
65                  70                  75                  80

Asp Asn Gln Leu Val Val Pro Ser Glu Gly Leu Tyr Leu Ile Tyr Ser
                85                  90                  95

Gln Val Leu Phe Lys Gly Gln Gly Cys Pro Ser Thr His Val Leu Leu
            100                 105                 110

Thr His Thr Ile Ser Arg Ile Ala Val Ser Tyr Gln Thr Lys Val Asn
        115                 120                 125

Leu Leu Ser Ala Ile Lys Ser Pro Cys Gln Arg Glu Thr Pro Glu Gly
130                 135                 140

Ala Glu Ala Lys Pro Trp Tyr Glu Pro Ile Tyr Leu Gly Gly Val Phe
145                 150                 155                 160

Gln Leu Glu Lys Gly Asp Arg Leu Ser Ala Glu Ile Asn Arg Pro Asp
                165                 170                 175

Tyr Leu Asp Phe Ala Glu Ser Gly Gln Val Tyr Phe Gly Ile Ile Ala
            180                 185                 190

Leu

<210> SEQ ID NO 4
<211> LENGTH: 12
<212> TYPE: PRT
<213> ORGANISM: Artificial Sequence
<220> FEATURE:
<223> OTHER INFORMATION: polypeptide substrate of TNF-alpha convertase
<220> FEATURE:
<221> NAME/KEY: MISC_FEATURE
<222> LOCATION: (1)..(1)
<223> OTHER INFORMATION: X is S that has been dinitrophenylated at the
      alpha amino group
<220> FEATURE:
<221> NAME/KEY: MISC_FEATURE
<222> LOCATION: (12)..(12)
<223> OTHER INFORMATION: X is R that has been amidated at the carboxyl
```

-continued terminus

<400> SEQUENCE: 4

Xaa Pro Leu Ala Gln Ala Val Arg Ser Ser Ser Xaa
1               5                      10

<210> SEQ ID NO 5
<211> LENGTH: 31
<212> TYPE: DNA
<213> ORGANISM: Artificial Sequence
<220> FEATURE:
<223> OTHER INFORMATION: primer

<400> SEQUENCE: 5
tagcggtacc gcccacactg cccggctgac c                                              31

<210> SEQ ID NO 6
<211> LENGTH: 34
<212> TYPE: DNA
<213> ORGANISM: Artificial Sequence
<220> FEATURE:
<223> OTHER INFORMATION: primer

<400> SEQUENCE: 6
caacaagctt accaccacct tgctgacact ggtc                                      34

<210> SEQ ID NO 7
<211> LENGTH: 32
<212> TYPE: DNA
<213> ORGANISM: Artificial Sequence
<220> FEATURE:
<223> OTHER INFORMATION: primer

<400> SEQUENCE: 7
actagaattc agagcatggg cagcgacccg ag                                          32

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
gcccttgaac acgaacatct cc                                                          22

<210> SEQ ID NO 9
<211> LENGTH: 31
<212> TYPE: DNA
<213> ORGANISM: Artificial Sequence
<220> FEATURE:
<223> OTHER INFORMATION: primer

<400> SEQUENCE: 9
actatctaga gccccctgag caccgttagc a                                              31

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
gccacagcct acccagcctc tc                                                          22

<210> SEQ ID NO 11
<211> LENGTH: 35
<212> TYPE: DNA
<213> ORGANISM: Artificial Sequence
<220> FEATURE:
<223> OTHER INFORMATION: primer

<400> SEQUENCE: 11
tagcggtacc acagttcact atgatcttac tcaca                                    35

<210> SEQ ID NO 12
<211> LENGTH: 35
<212> TYPE: DNA
<213> ORGANISM: Artificial Sequence
<220> FEATURE:
<223> OTHER INFORMATION: primer

<400> SEQUENCE: 12
tagcaagctt agcctgctcc tagctaggaa acagc                                    35

<210> SEQ ID NO 13
<211> LENGTH: 28
<212> TYPE: DNA
<213> ORGANISM: Artificial Sequence
<220> FEATURE:
<223> OTHER INFORMATION: primer

<400> SEQUENCE: 13
actaggtacc atgcgactca ccgtgctg                                            28

<210> SEQ ID NO 14
<211> LENGTH: 29
<212> TYPE: DNA
<213> ORGANISM: Artificial Sequence
<220> FEATURE:
<223> OTHER INFORMATION: primer

<400> SEQUENCE: 14
cacaagcttg ctcaccgccc cgccgccct                                           29

<210> SEQ ID NO 15
<211> LENGTH: 32
<212> TYPE: DNA
<213> ORGANISM: Artificial Sequence
<220> FEATURE:
<223> OTHER INFORMATION: primer

<400> SEQUENCE: 15
ctacggtacc acaatgaagt ttcttctaat ac                                       32

<210> SEQ ID NO 16
<211> LENGTH: 28
<212> TYPE: DNA
<213> ORGANISM: Artificial Sequence
<220> FEATURE:
<223> OTHER INFORMATION: primer

<400> SEQUENCE: 16
cttctctaga ctaacaacca aaccagct                                            28

<210> SEQ ID NO 17
<211> LENGTH: 36
<212> TYPE: DNA
<213> ORGANISM: Artificial Sequence
<220> FEATURE:
<223> OTHER INFORMATION: primer

<400> SEQUENCE: 17
cttccgggta cccggaagat ggtgttgctg agagtg                          36

<210> SEQ ID NO 18
<211> LENGTH: 36
<212> TYPE: DNA
<213> ORGANISM: Artificial Sequence
<220> FEATURE:
<223> OTHER INFORMATION: primer

<400> SEQUENCE: 18
cgttaaaagc ttttaacgtc tcatgtgtcc catctg                          36

<210> SEQ ID NO 19
<211> LENGTH: 31
<212> TYPE: DNA
<213> ORGANISM: Artificial Sequence
<220> FEATURE:
<223> OTHER INFORMATION: primer

<400> SEQUENCE: 19
accgggatcc atgagcactg aaagcatgat c                               31

<210> SEQ ID NO 20
<211> LENGTH: 32
<212> TYPE: DNA
<213> ORGANISM: Artificial Sequence
<220> FEATURE:
<223> OTHER INFORMATION: primer

<400> SEQUENCE: 20
gtctggatcc gaatcccagg tttcgaagtg gt                              32

<210> SEQ ID NO 21
<211> LENGTH: 2352
<212> TYPE: DNA
<213> ORGANISM: Homo sapiens

<400> SEQUENCE: 21
atgccacata ctttgtggat ggtgtgggtc ttggggtca tcatcagcct ctccaaggaa     60
gaatcctcca atcaggcttc tctgtcttgt gaccgcaatg gtatctgcaa gggcagctca    120
ggatctttaa actccattcc ctcagggctc acagaagctg taaaaagcct tgacctgtcc    180
aacaacagga tcacctacat tagcaacagt gacctacaga ggtgtgtgaa cctccaggct    240
ctggtgctga catccaatgg aattaacaca atagaggaag attcttttc ttccctgggc    300 agtcttgaac atttagactt atcctataat tacttatcta atttatcgtc ttcctggttc    360 aagcccctt cttctttaac attcttaaac ttactgggaa atccttacaa aaccctaggg    420
gaaacatctc ttttttctca tctcacaaaa ttgcaaatcc tgagagtggg aaatatggac    480
accttcacta agattcaaag aaaagatttt gctggactta ccttccttga ggaacttgag    540
attgatgctt cagatctaca gagctatgag ccaaaaagtt tgaagtcaat tcagaatgta    600
agtcatctga tccttcatat gaagcagcat atttactgc tggagatttt tgtagatgtt    660
acaagttccg tggaatgttt ggaactgcga gatactgatt tggacacttt ccatttttca    720
gaactatcca ctggtgaaac aaattcattg attaaaaagt ttacatttag aaatgtgaaa    780
atcaccgatg aaagtttgtt tcaggttatg aaactttga atcagatttc tggattgtta    840
gaattagagt ttgatgactg taccttaat ggagttggta attttagagc atctgataat    900

-continued

```
gacagagtta tagatccagg taaagtggaa acgttaacaa tccggaggct gcatattcca    960
aggttttact tattttatga tctgagcact ttatattcac ttacagaaag agttaaaaga   1020
atcacagtag aaaacagtaa agtttttctg gttccttgtt tactttcaca acatttaaaa   1080

tcattagaat acttggatct cagtgaaaat ttgatggttg aagaatactt gaaaaattca   1140
gcctgtgagg atgcctggcc ctctctacaa actttaattt taaggcaaaa tcatttggca   1200
tcattggaaa aaaccggaga gactttgctc actctgaaaa acttgactaa cattgatatc   1260
agtaagaata gttttcattc tatgcctgaa acttgtcagt ggccagaaaa gatgaaatat   1320
ttgaacttat ccagcacacg aatacacagt gtaacaggct gcattcccaa gacactggaa   1380
attttagatg ttagcaacaa caatctcaat ttattttctt tgaatttgcc gcaactcaaa   1440
gaactttata tttccagaaa taagttgatg actctaccag atgcctccct cttacccatg   1500
ttactagtat tgaaaatcag taggaatgca ataactacgt tttctaagga gcaacttgac   1560
tcatttcaca cactgaagac tttggaagct ggtggcaata acttcatttg ctcctgtgaa   1620
ttcctctcct tcactcagga gcagcaagca ctggccaaag tcttgattga ttggccagca   1680
aattacctgt gtgactctcc atcccatgtg cgtggccagc aggttcagga tgtccgcctc   1740
tcggtgtcgg aatgtcacag gatagcactg gtgtctggca tgtgctgtgc tctgttcctg   1800
ctgatcctgc tcacgggggt cctgtgccac cgtttccatg gcctgtggta tatgaaaatg   1860
atgtgggcct ggctccaggc caaaaggaag cccaggaaag ctcccagcag gaacatatgt   1920
tatgatgcat ttgtttctta cagtgagcgg gatgcctact gggtggagaa cctaatggtc   1980
caggagctgg agaacttcaa tccccccttc aagttgtgtc ttcataagcg ggacttcatt   2040
cctggcaagt ggatcattga caatatcatt gactccattg aaaagagcca caaaactgtc   2100
tttgtgcttt ctgaaaactt tgtgaagagt gagtggtgca agtatgaact ggacttctcc   2160
catttccgtc tttttgatga gaacaatgat gctgccattc tcattcttct ggagcccatt   2220
gagaaaaaag ccattcccca gcgcttctgc aagctgcgga agataatgaa caccaagacc   2280
tacctggagt ggcccatgga cgaggctcag cgggaaggat tttgggtaaa tctgagagct   2340
gcgataaagt cc                                                       2352
```

```

<210> SEQ ID NO 22
<211> LENGTH: 233
<212> TYPE: PRT
<213> ORGANISM: Homo sapiens
<220> FEATURE:
<221> NAME/KEY: MISC_FEATURE
<222> LOCATION: (63)..(63)
<223> OTHER INFORMATION: X may be either F or S

<400> SEQUENCE: 22

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Xaa Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95
```

```
Gln Ala Glu Gly Gln Leu Gln Trp Leu Asn Arg Arg Ala Asn Ala Leu
                100                 105                 110
Leu Ala Asn Gly Val Glu Leu Arg Asp Asn Gln Leu Val Val Pro Ser
            115                 120                 125
Glu Gly Leu Tyr Leu Ile Tyr Ser Gln Val Leu Phe Lys Gly Gln Gly
        130                 135                 140
Cys Pro Ser Thr His Val Leu Leu Thr His Thr Ile Ser Arg Ile Ala
145                 150                 155                 160
Val Ser Tyr Gln Thr Lys Val Asn Leu Leu Ser Ala Ile Lys Ser Pro
                165                 170                 175
Cys Gln Arg Glu Thr Pro Glu Gly Ala Glu Ala Lys Pro Trp Tyr Glu
            180                 185                 190
Pro Ile Tyr Leu Gly Gly Val Phe Gln Leu Glu Lys Gly Asp Arg Leu
        195                 200                 205
Ser Ala Glu Ile Asn Arg Pro Asp Tyr Leu Asp Phe Ala Glu Ser Gly
    210                 215                 220
Gln Val Tyr Phe Gly Ile Ile Ala Leu
225                 230
```

<210> SEQ ID NO 23
<211> LENGTH: 784
<212> TYPE: PRT
<213> ORGANISM: Homo sapiens

<400> SEQUENCE: 23

```
Met Pro His Thr Leu Trp Met Val Trp Val Leu Gly Val Ile Ile Ser
1               5                   10                  15
Leu Ser Lys Glu Glu Ser Ser Asn Gln Ala Ser Leu Ser Cys Asp Arg
                20                  25                  30
Asn Gly Ile Cys Lys Gly Ser Ser Gly Ser Leu Asn Ser Ile Pro Ser
            35                  40                  45
Gly Leu Thr Glu Ala Val Lys Ser Leu Asp Leu Ser Asn Asn Arg Ile
        50                  55                  60
Thr Tyr Ile Ser Asn Ser Asp Leu Gln Arg Cys Val Asn Leu Gln Ala
65                  70                  75                  80
Leu Val Leu Thr Ser Asn Gly Ile Asn Thr Ile Glu Glu Asp Ser Phe
                85                  90                  95
Ser Ser Leu Gly Ser Leu Glu His Leu Asp Leu Ser Tyr Asn Tyr Leu
                100                 105                 110
Ser Asn Leu Ser Ser Ser Trp Phe Lys Pro Leu Ser Ser Leu Thr Phe
            115                 120                 125
Leu Asn Leu Leu Gly Asn Pro Tyr Lys Thr Leu Gly Glu Thr Ser Leu
        130                 135                 140
Phe Ser His Leu Thr Lys Leu Gln Ile Leu Arg Val Gly Asn Met Asp
145                 150                 155                 160
Thr Phe Thr Lys Ile Gln Arg Lys Asp Phe Ala Gly Leu Thr Phe Leu
                165                 170                 175
Glu Glu Leu Glu Ile Asp Ala Ser Asp Leu Gln Ser Tyr Glu Pro Lys
            180                 185                 190
Ser Leu Lys Ser Ile Gln Asn Val Ser His Leu Ile Leu His Met Lys
        195                 200                 205
Gln His Ile Leu Leu Leu Glu Ile Phe Val Asp Val Thr Ser Ser Val
    210                 215                 220
Glu Cys Leu Glu Leu Arg Asp Thr Asp Leu Asp Thr Phe His Phe Ser
```

-continued

```
                225                 230                 235                 240
Glu Leu Ser Thr Gly Glu Thr Asn Ser Leu Ile Lys Lys Phe Thr Phe
                    245                 250                 255
Arg Asn Val Lys Ile Thr Asp Glu Ser Leu Phe Gln Val Met Lys Leu
                260                 265                 270
Leu Asn Gln Ile Ser Gly Leu Leu Glu Leu Glu Phe Asp Asp Cys Thr
                275                 280                 285
Leu Asn Gly Val Gly Asn Phe Arg Ala Ser Asp Asn Asp Arg Val Ile
                290                 295                 300
Asp Pro Gly Lys Val Glu Thr Leu Thr Ile Arg Arg Leu His Ile Pro
305                 310                 315                 320
Arg Phe Tyr Leu Phe Tyr Asp Leu Ser Thr Leu Tyr Ser Leu Thr Glu
                    325                 330                 335
Arg Val Lys Arg Ile Thr Val Glu Asn Ser Lys Val Phe Leu Val Pro
                340                 345                 350
Cys Leu Leu Ser Gln His Leu Lys Ser Leu Glu Tyr Leu Asp Leu Ser
                355                 360                 365
Glu Asn Leu Met Val Glu Glu Tyr Leu Lys Asn Ser Ala Cys Glu Asp
370                 375                 380
Ala Trp Pro Ser Leu Gln Thr Leu Ile Leu Arg Gln Asn His Leu Ala
385                 390                 395                 400
Ser Leu Glu Lys Thr Gly Glu Thr Leu Leu Thr Leu Lys Asn Leu Thr
                    405                 410                 415
Asn Ile Asp Ile Ser Lys Asn Ser Phe His Ser Met Pro Glu Thr Cys
                420                 425                 430
Gln Trp Pro Glu Lys Met Lys Tyr Leu Asn Leu Ser Ser Thr Arg Ile
                435                 440                 445
His Ser Val Thr Gly Cys Ile Pro Lys Thr Leu Glu Ile Leu Asp Val
                450                 455                 460
Ser Asn Asn Asn Leu Asn Leu Phe Ser Leu Asn Leu Pro Gln Leu Lys
465                 470                 475                 480
Glu Leu Tyr Ile Ser Arg Asn Lys Leu Met Thr Leu Pro Asp Ala Ser
                    485                 490                 495
Leu Leu Pro Met Leu Leu Val Leu Lys Ile Ser Arg Asn Ala Ile Thr
                500                 505                 510
Thr Phe Ser Lys Glu Gln Leu Asp Ser Phe His Thr Leu Lys Thr Leu
                515                 520                 525
Glu Ala Gly Gly Asn Asn Phe Ile Cys Ser Cys Glu Phe Leu Ser Phe
                530                 535                 540
Thr Gln Glu Gln Gln Ala Leu Ala Lys Val Leu Ile Asp Trp Pro Ala
545                 550                 555                 560
Asn Tyr Leu Cys Asp Ser Pro Ser His Val Arg Gly Gln Gln Val Gln
                    565                 570                 575
Asp Val Arg Leu Ser Val Ser Glu Cys His Arg Ile Ala Leu Val Ser
                580                 585                 590
Gly Met Cys Cys Ala Leu Phe Leu Leu Ile Leu Leu Thr Gly Val Leu
                595                 600                 605
Cys His Arg Phe His Gly Leu Trp Tyr Met Lys Met Met Trp Ala Trp
                610                 615                 620
Leu Gln Ala Lys Arg Lys Pro Arg Lys Ala Pro Ser Arg Asn Ile Cys
625                 630                 635                 640
Tyr Asp Ala Phe Val Ser Tyr Ser Glu Arg Asp Ala Tyr Trp Val Glu
                    645                 650                 655
```

```
Asn Leu Met Val Gln Glu Leu Glu Asn Phe Asn Pro Pro Phe Lys Leu
            660                 665                 670

Cys Leu His Lys Arg Asp Phe Ile Pro Gly Lys Trp Ile Ile Asp Asn
        675                 680                 685

Ile Ile Asp Ser Ile Glu Lys Ser His Lys Thr Val Phe Val Leu Ser
        690                 695                 700

Glu Asn Phe Val Lys Ser Glu Trp Cys Lys Tyr Glu Leu Asp Phe Ser
705                 710                 715                 720

His Phe Arg Leu Phe Asp Glu Asn Asn Asp Ala Ala Ile Leu Ile Leu
                725                 730                 735

Leu Glu Pro Ile Glu Lys Lys Ala Ile Pro Gln Arg Phe Cys Lys Leu
            740                 745                 750

Arg Lys Ile Met Asn Thr Lys Thr Tyr Leu Glu Trp Pro Met Asp Glu
            755                 760                 765

Ala Gln Arg Glu Gly Phe Trp Val Asn Leu Arg Ala Ala Ile Lys Ser
770                 775                 780
```

MAMMALIAN TNF-α CONVERTASES

This application is a continuation of application Ser. No. 09/982,308, flied Oct. 17, 2001, now U.S. Pat. No. 6,531,290, which is a divisional of application Ser. No. 09/156,163, flied Sep. 17, 1998, now U.S. Pat. No. 6,319,681, which is a divisional of application Ser. No. 08/889,909, filed Jul. 10, 1997, now U.S. Pat. No. 5,853,977, which in turn claims priority under 35 U.S.C. § 119(e) to Application Ser. No. 60/021,710, filed Jul. 12, 1996.

TECHNICAL FIELD

The present invention relates to mammalian tumor necrosis factor-α (TNF-α) convertase enzymes. More particularly, it relates to bovine, human and other TNF-α convertases, isolated nucleic acids and recombinant vectors encoding the enzymes, methods for making the enzymes, fragments or fusion proteins thereof using recombinant DNA methodology or chemical synthesis, and to methods for using the enzymes in screening systems to identify TNF-α convertase inhibitors for the treatment of various diseases, and nucleic acids encoding a TNF-α convertase. This invention further relates to antibodies, both polyclonal and monoclonal, which specifically bind to the TNF-α convertases, and to fragments and fusion proteins of the TNF-α convertases of the invention.

BACKGROUND OF THE INVENTION

TNF-α, also known as cachectin, is a 17 kDa (kilodalton) protein produced by cells of the monocyte/macrophage lineage, and by other cells. A variety of biological effects, both beneficial and deleterious, have been attributed to TNF-α. TNF-α is beneficial, e.g., in that it is believed to be a part of host anti-tumor defenses. It also produces detrimental effects, however, including, e.g., cardiovascular (shock, ARDS, capillary leakage syndrome), renal (nephritis, acute tubal necrosis), and gastrointestinal (ischemia, colitis, hepatic necrosis) effects, and effects on the central nervous system (fever, anorexia, altered pituitary hormone secretion). In view of the foregoing, a consensus view has developed that TNF-α is a key mediator of inflammation (including inflammatory diseases such as arthritis) and mammalian responses to injury, invasion by pathogens, and neoplasia.

The biosynthesis of human TNF-α proceeds by way of a membrane-bound precursor containing 233 amino acid residues [Wang et al., *Science* 228:149–154 (1985); Muller et al., *Nature* 335:265–267 (1987)], which is processed during cellular activation by cleavage of a 76-residue peptide to produce the mature, secreted form of TNF-α. The enzyme(s) responsible for this cleavage, called TNF-α convertase, has until the present invention been elusive for most mammalian species.

A putative TNF-α convertase, called PR-3, has been isolated and cloned from human neutrophils, and it has been suggested that this enzyme can be used in screens to identify TNF-α convertase inhibitors. See International Patent Applications Publication Numbers WO 94/00555 and WO 95/24501. This enzyme, however, is not believed to be the physiologically relevant human TNF-α convertase because it is a serine protease, whereas the relevant enzyme is believed to be a metalloproteinase. Moreover, the source of the serine protease, neutrophils, is not believed to be important in the production of TNF-α, and the serine protease does not cleave the precursor form of TNF-α (proTNF-α) at the point expected for the physiologically relevant human enzyme.

Mohler et al. [*Nature* 70:218 (1994)] have partially purified another TNF-α convertase from the human monocytic cell line THP-1. This preparation, however, was very impure, and little could be said about the nature of the TNF-α convertase in the crude protein mixture of Mohler et al.

In view of the important role of TNF-α in many disease processes, there is a need for agents that can selectively block the biosynthesis of mature, secreted TNF-α. The search for such agents would be greatly facilitated by the availability of substantially pure mammalian TNF-α convertases.

SUMMARY OF THE INVENTION

The present invention fills the foregoing need by providing materials and methods for identifying specific inhibitors of TNF-α convertase. More particularly, this invention provides substantially pure mammalian TNF-α convertases capable of converting proTNF-α to the mature, secreted form. This invention further provides isolated or recombinant nucleic acids encoding mammalian TNF-α convertases, and recombinant vectors and host cells comprising such nucleic acids.

This invention further provides a method for making a mammalian TNF-α convertase, comprising culturing a host cell comprising a nucleic acid encoding a mammalian TNF-α convertase under conditions in which the nucleic acid is expressed. In some embodiments, the method further comprises isolation of the TNF-α convertase from the culture.

This invention also provides polypeptides comprising a fragment of a TNF-α convertase having an amino acid sequence corresponding to the sequence of at least about 8 contiguous residues of the complete enzyme sequence. Preferably, the polypeptides comprise at least about 12, more preferably at least about 20, and most preferably at least about 30 such residues.

Still further, this invention provides fusion proteins comprising a TNF-α convertase or a polypeptide thereof covalently linked to a fusion partner.

The present invention also provides antibodies, both polyclonal and monoclonal, that specifically bind to one or more of the TNF-α convertases or to a polypeptide thereof. Also provided are anti-idiotypic antibodies, both monoclonal and polyclonal, which specifically bind to the foregoing antibodies.

This invention still further provides a method of treatment comprising administering to a mammal afflicted with a medical condition caused or mediated by TNF-α, an effective amount of an antibody, or an antigen-binding fragment thereof, that specifically binds to a mammalian TNF-α convertase, and pharmaceutical compositions comprising such antibodies or fragments and pharmaceutically acceptable carriers.

The present invention also provides a method for identifying an inhibitor of a mammalian TNF-α convertase, comprising:
(a) contacting a mammalian TNF-α convertase in the presence of substrate with a sample to be tested for the presence of an inhibitor of the convertase; and
(b) measuring the rate of cleavage of the substrate;
whereby an inhibitor of the TNF-α convertase in the sample is identified by measuring substantially reduced cleavage of the substrate, compared to what would be measured in the absence of such inhibitor.

In a preferred embodiment, the contacting of the convertase with the sample in the presence of substrate occurs on the surface of a mammalian host cell comprising one or more nucleic acids encoding a mammalian TNF-α convertase and a substrate of the convertase.

BRIEF DESCRIPTION OF THE FIGURES

The present invention can be more readily understood by reference to the following Description and Examples, and to the accompanying Figures, in which.

DESCRIPTION OF THE INVENTION

Figure 1:
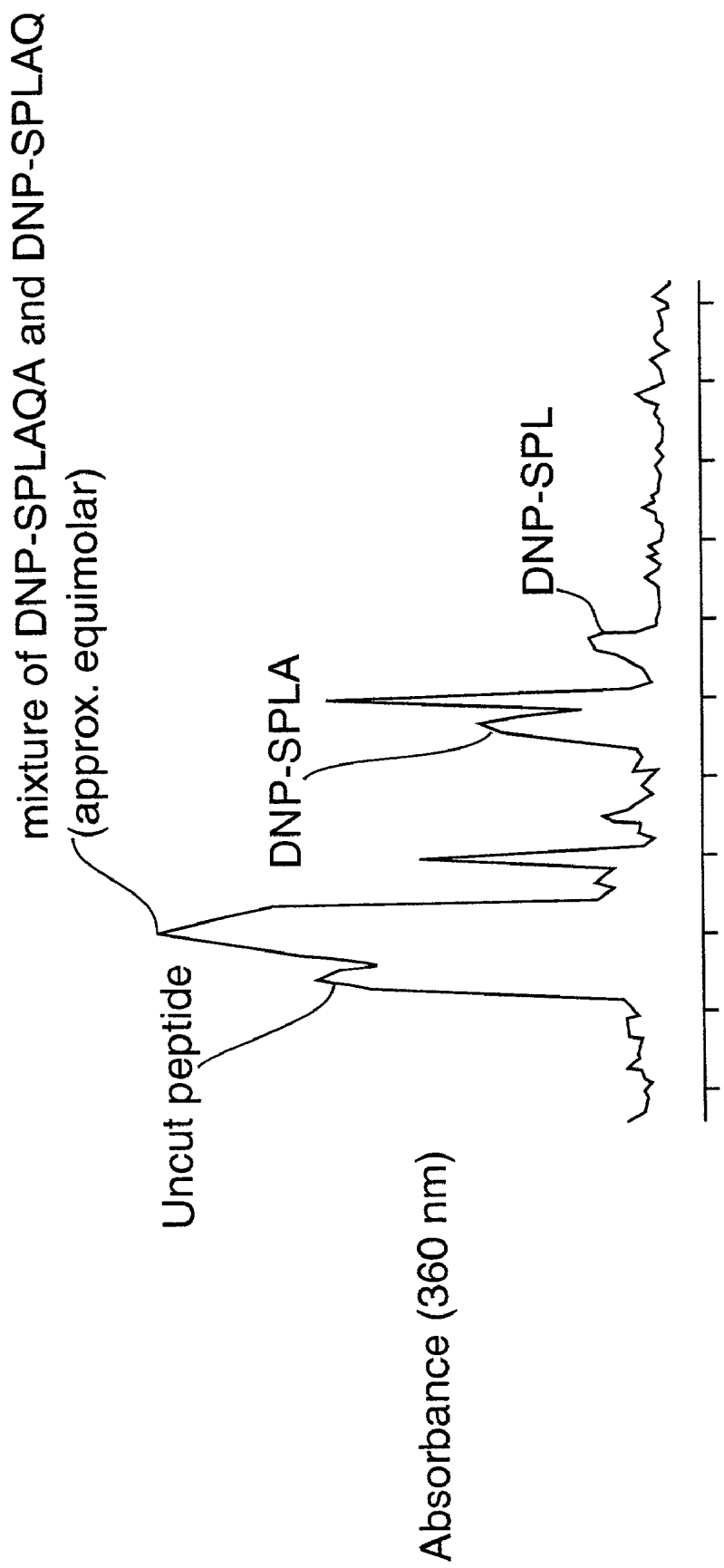
FIG. 1 is an elution profile from an HPLC column showing DNP-proTNF-α cleavage products.

All references cited herein are hereby incorporated in their entirety by reference. As used herein, the terms "proteinase" and "protease" are intended to mean the same thing and are used interchangeably. So too are the terms "assay(s)" and "screen(s)".

Characterization of TNF-α Convertases

The mammalian TNF-α convertases of the present invention are functionally characterized by an ability to process, through proteolytic cleavage, the conversion of the membrane-bound form of a precursor form of TNF-α, referred to herein as "proTNF-α", to the soluble, mature form. This processing entails cleavage of the first 76 amino-terminal residues of the human precursor protein, the entire sequence of which is defined in the Sequence Listing by SEQ ID NO: 1. This sequence, taken from *Human Cytokines*, B. Aggarwal and J. Gutterman, Eds., 1992, Blackwell Scientific Publications, Oxford, pp. 276–277, is in agreement with the Swiss-Prot sequence, Accession Code: Swiss-Prot P01375. There is a conflict, however, with the corresponding GenBank sequence [Accession No. M10988; Wang et al., *Science* 228:149 (1985)], which has a serine residue at position −14, instead of the phenylalanine residue shown at that position in SEQ ID NO: 1.

Regardless of whether one or both of these sequences is correct, as might be the case with allelic or polymorphic variants, cleavage of proTNF-α by the TNF-α convertases of this invention occurs at an Ala-Val peptide bond, resulting in mature human TNF-α having a valine residue at the amino terminus (i.e., beginning with the Val residue at position 1 of SEQ ID NO: 1).

The foregoing cleavage point is different from that observed for the serine protease PR-3 mentioned above. Robache-Gallea et al. [*J. Biol. Chem.* 270:23688 (1995)] have shown that the serine protease cleaves between $Val^1$ and $Arg^2$ of SEQ ID NO: 1, thereby producing a mature form of TNF-α having an N-terminal arginine residue.

The mammalian TNF-α convertases of the present invention are further characterized by their presence in cells that make TNF-α. They may be present in other cells as well, however, and may even be ubiquitously expressed. Control could be exerted at the level of transcription of the proTNF-α message, or specific controllers of the TNF-α convertases could be present in different cell types. It is also not necessary that the TNF-α convertases cleave and process only proTNF-α; they could have other substrates as well. It also may be that different TNF-α convertases process proTNF-α in different cell types. Thus, one convertase might carry out processing in T and NK cells, while a different enzyme might function in macrophages. It therefore may not be necessary that a given TNF-α convertase be present in all cell types that make TNF-α.

But apart from the requirement that a TNF-α convertase of this invention be present in at least one type of cell that makes TNF-α, whether the other possibilities discussed in the foregoing paragraph are correct or not is not essential to the invention.

Tryptic digestion followed by amino acid sequencing of a peptide from a TNF-α convertase isolated from bovine spleen revealed that enzyme to be further characterized by an amino acid sequence comprising a sequence substantially as follows:

Met-Asn-Ser-Leu-Leu-Gly/Asp-Ser-Ala-Pro (SEQ ID NO: 2).

This bovine enzyme is further characterized by behavior observed in various chromatographic systems during purification, as is described in detail in the Example below, and by an apparent molecular weight in SDS-PAGE under reducing conditions of about 65 kDa.

The present invention also encompasses another bovine TNF-α convertase and enzymes from other mammalian species, including human TNF-α convertases.

Some general properties of TNF-α convertases as defined in this invention are as follows:

(1) Inhibited by ethylenediaminetetraacetic acid (EDTA), dithiothreitol (DTT), 1,10-phenanthroline and/or α-2 macroglobulin.

(2) Not inhibited by serine, cysteine and acid protease inhibitors, such as 100 μM captopril, 300 μM phosphoramidon, 100 μM thiorphan, 100 μM dichloroisocoumarin (DCI), 1 mM iodoacetic acid (IAA), 1 μg/ml tissue inhibitor of metalloproteases-1 (TIMP-1), 1 μg/ml soybean trypsin inhibitor (SBTI), 1 mM methoxysuccinyl-Ala-Ala-Pro-Val-chloromethylketone (AAPV) and 100 μM trans-epoxysuccinyl-L-leucylamino (4-guanidino)-butane (E64; a thiol protease inhibitor).

(3) Membrane-bound on THP-1 cells and on other monocytic-type cells and cell lines.

(4) Cleave human pro-TNF-α at an Ala-Val peptide bond, to produce soluble, mature TNF-α.

The proteins of the present invention are useful in rational drug discovery screens for the identification of compounds that selectively block the conversion of proTNF-α to soluble, mature TNF-α. They have this utility because when introduced into cells used in the screens, e.g., by transfection of nucleic acids encoding the proteins, they produce TNF-α convertase activity which can act on an appropriate substrate as described herein. Inhibitors can be identified by measuring inhibition of this activity.

Some Definitions

As used herein, the term "bovine TNF-α convertase" in one embodiment means an enzyme having the above-mentioned subsequence and purification characteristics, or a significant fragment of such a protein which substantially retains the proteolytic activity and specificity disclosed herein. In another embodiment, "bovine TNF-α convertase" means bovine ADAM 10 [GenBank Accession No. Z21961;

Wolfsberg et al., *J. Cell. Biol.* 131:275 (1995)], which the present inventors have surprisingly found is a TNF-α convertase. It also refers to a bovine-derived enzyme exhibiting similar enzymatic activity which specifically binds to an antibody elicited against either of the bovine TNF-α convertases, or to a proteolytically active fragment from one of those enzymes. Such antibodies typically bind to a bovine or other TNF-α convertase with high affinity, e.g., with an affinity constant of at least about 100 nM, usually better than about 30 nM, preferably better than about 10 nM, and more preferably better than about 3 nM.

Because bovine ADAM 10 is a TNF-α convertase and a comparison of its amino acid sequence with available sequence information on human ADAM 10 shows the two proteins to be 96% homologous, the present inventors believe that human ADAM 10 is also a TNF-α convertase as defined herein.

Surprisingly, the present inventors have also discovered that the human membrane-type metalloproteases MT-MMP1 [Sato et al., *Nature* 370:61 (1994)], MT-MMP2 [Will et al., *Eur. J. Biochem.* 231:602 (1995)] and MT-MMP3 [Takino et al., *J. Biol. Chem.* 270:23013 (1995)] are also TNF-α convertases as defined herein.

The present inventors have further cloned a cDNA encoding a novel human protein. When transfected into mammalian cells otherwise incapable of processing human proTNF-α to soluble, mature TNF-α, this protein produces such processing. The sequence of this DNA, together with the predicted amino acid sequence, is substantially as defined in the Sequence Listing by SEQ ID NO: 21.

As used herein, the term "polypeptide" means a fragment or segment, e.g., of a TNF-α convertase which comprises a subsequence of the complete amino acid sequence of the enzyme containing at least about 8, preferably at least about 12, more preferably at least about 20, and most preferably at least about 30 or more contiguous amino acid residues, up to and including the total number of residues in the complete enzyme.

The polypeptides of the invention can comprise any part of the complete sequence of a TNF-α convertase. Thus, although they could be produced by proteolytic cleavage of an intact enzyme, they can also be made by chemical synthesis or by the application of recombinant DNA technology and are not limited to polypeptides delineated by proteolytic cleavage sites.

The term "analog(s)" means a TNF-α convertase which has been modified by deletion, addition, modification or substitution of one or more amino acid residues in the wild-type enzyme. It encompasses allelic and polymorphic variants, and also muteins and fusion proteins which comprise all or a significant part of a TNF-α convertase, e.g., covalently linked via a side-chain group or terminal residue to a different protein, polypeptide or moiety (fusion partner).

Some amino acid substitutions are preferably "conservative", with residues replaced with physicochemically similar residues, such as Gly/Ala, Asp/Glu, Val/Ile/Leu, Lys/Arg, Asn/Gln and Phe/Trp/Tyr. Analogs having such conservative substitutions typically retain substantial proteolytic activity. Other analogs, which have non-conservative substitutions such as Asn/Glu, Val/Tyr and His/Glu, may substantially lack proteolytic activity. Nevertheless, such analogs are useful because they can be used as antigens to elicit production of antibodies in an immunologically competent host. Because these analogs retain many of the epitopes (antigenic determinants) of the wild-type enzymes from which they are derived, many antibodies produced against them can also bind to the active-conformation or denatured wild-type enzymes. Accordingly, the antibodies can be used, e.g., for the immunopurification or immunoassay of the wild-type enzymes.

Whether a particular analog exhibits convertase activity can be determined by routine experimentation as described herein.

Some analogs are truncated variants in which residues have been successively deleted from the amino- and/or carboxyl-termini, while substantially retaining the characteristic proteolytic activity.

Modifications of amino acid residues may include but are not limited to aliphatic esters or amides of the carboxyl terminus or of residues containing carboxyl side chains, O-acyl derivatives of hydroxyl group-containing residues, and N-acyl derivatives of the amino-terminal amino acid or amino-group containing residues, e.g., lysine or arginine.

This invention also encompasses physical variants having substantial amino acid sequence homology with the amino acid sequences of the TNF-α convertases or polypeptides. In this invention, amino acid sequence homology, or sequence identity, is determined by optimizing residue matches and, if necessary, by introducing gaps as required. Homologous amino acid sequences are typically intended to include natural allelic, polymorphic and interspecies variations in each respective sequence.

Typical homologous proteins or peptides will have from 25–100% homology (if gaps can be introduced) to 50–100% homology (if conservative substitutions are included), with the amino acid sequence of the TNF-α convertases. Primate species convertases are of particluar interest.

Observed homologies will typically be at least about 35%, preferably at least about 50%, more preferably at least about 75%, and most preferably at least about 85% or more. See Needleham et al., *J. Mol. Biol.* 48:443–453 (1970); Sankoff et al. in *Time Warps, String Edits, and Macromolecules: The Theory and Practice of Sequence Comparison*, 1983, Addison-Wesley, Reading, Mass.; and software packages from IntelliGenetics, Mountain View, Calif., and the University of Wisconsin Genetics Computer Group, Madison, Wis.

Glycosylation variants include, e.g., analogs made by modifying glycosylation patterns during synthesis and processing in various alternative eukaryotic host expression systems, or during further processing steps. Particularly preferred methods for producing glycosylation modifications include exposing the TNF-α convertases to glycosylating enzymes derived from cells which normally carry out such processing, such as mammalian glycosylation enzymes. Alternatively, deglycosylation enzymes can be used to remove carbohydrates attached during production in eukaryotic expression systems.

Other analogs are TNF-α convertases containing modifications, such as incorporation of unnatural amino acid residues, or phosphorylated amino acid residues such as phosphotyrosine, phosphoserine or phosphothreonine residues. Other potential modifications include sulfonation, biotinylation, or the addition of other moieties, particularly those which have molecular shapes similar to phosphate groups.

Analogs of TNF-α convertases can be prepared by chemical synthesis or by using site-directed mutagenesis [Gillman et al., *Gene* 8:81 (1979); Roberts et al., *Nature* 328:731 (1987) or Innis (Ed.), 1990, *PCR Protocols: A Guide to Methods and Applications*, Academic Press, New York, N.Y.] or the polymerase chain reaction method [PCR; Saiki et al., *Science* 239:487 (1988)], as exemplified by Daugherty et al. [*Nucleic Acids Res.* 19:2471 (1991)] to modify nucleic acids encoding the complete enzymes. Adding epitope tags for purification or detection of recombinant products is envisioned.

General techniques for nucleic acid manipulation and expression are described generally, e.g., in Sambrook, et al., *Molecular Cloning: A Laboratory Manual* (2d ed.), 1989, Vols. 1–3, Cold Spring Harbor Laboratory. Techniques for the synthesis of polypeptides are described, for example, in Merrifield, *J. Amer. Chem. Soc.* 85:2149 (1963); Merrifield, *Science* 232:341 (1986); and Atherton et al., *Solid Phase Peptide Synthesis: A Practical Approach,* 1989, IRL Press, Oxford.

Still other analogs are prepared by the use of agents known in the art for their usefulness in cross-linking proteins through reactive side groups. Preferred derivatization sites with cross-linking agents are free amino groups, carbohydrate moieties and cysteine residues.

Substantial retention of proteolytic activity by the foregoing analogs of the TNF-α convertases typically entails retention of at least about 50%, preferably at least about 75%, more preferably at least about 80%, and most preferably at least about 90% of the proTNF-α processing activity and/or specificity of the corresponding wild-type enzyme.

As used herein, the term "isolated nucleic acid" means a nucleic acid such as an RNA or DNA molecule, or a mixed polymer, which is substantially separated from other components that are normally found in cells or in recombinant DNA expression systems. These components include but are not limited to ribosomes, polymerases, serum components, and flanking genomic sequences. The term thus embraces a nucleic acid which has been removed from its naturally occurring environment, and includes recombinant or cloned DNA isolates and chemically synthesized analogs or analogs biologically synthesized by heterologous systems. A substantially pure molecule includes isolated forms of the molecule.

An isolated nucleic acid will generally be a homogeneous composition of molecules but may, in some embodiments, contain minor heterogeneity. Such heterogeneity is typically found at the ends of nucleic acid coding sequences or in regions not critical to a desired biological function or activity.

A "recombinant nucleic acid" is defined either by its method of production or- structure. Some recombinant nucleic acids are thus made by the use of recombinant DNA techniques which involve human intervention, either in manipulation or selection. Others are made by fusing two fragments not naturally contiguous to each other. Engineered vectors are encompassed, as well as nucleic acids comprising sequences derived using any synthetic oligonucleotide process.

For example, a wild-type codon may be replaced with a redundant codon encoding the same amino acid residue or a conservative substitution, while at the same time introducing or removing a nucleic acid sequence recognition site. Similarly, nucleic acid segments encoding desired functions may be fused to generate a single genetic entity encoding a desired combination of functions not found together in nature. Although restriction enzyme recognition sites are often the target of such artificial manipulations, other site-specific targets, e.g., promoters, DNA replication sites, regulation sequences, control sequences, or other useful features may be incorporated by design. Sequences encoding epitope tags for detection or purification as described above may also be incorporated.

A nucleic acid "fragment" is defined herein as a nucleotide sequence comprising at least about 17, generally at least about 25, preferably at least about 35, more preferably at least about 45, and most preferably at least about 55 or more contiguous nucleotides.

This invention further encompasses recombinant DNA molecules and fragments having sequences that are identical or highly homologous to those described herein. The nucleic acids of the invention may be operably linked to DNA segments which control transcription, translation, and DNA replication.

"Homologous nucleic acid sequences" are those which when aligned and compared exhibit significant similarities. Standards for homology in nucleic acids are either measures for homology generally used in the art by sequence comparison or based upon hybridization conditions, which are described in greater detail below.

Substantial nucleotide sequence homology is observed when there is identity in nucleotide residues in two sequences (or in their complementary strands) when optimally aligned to account for nucleotide insertions or deletions, in at least about 50%, preferably in at least about 75%, more preferably in at least about 90%, and most preferably in at least about 95% of the aligned nucleotides.

Substantial homology also exists when one sequence will hybridize under selective hybridization conditions to another. Typically, selective hybridization will occur when there is at least about 55% homology over a stretch of at least about 30 nucleotides, preferably at least about 65% over a stretch of at least about 25 nucleotides, more preferably at least about 75%, and most preferably at least about 90% over about 20 nucleotides. See, e.g., Kanehisa, *Nucleic Acids Res.* 12:203 (1984).

The lengths of such homology comparisons may encompass longer stretches and in certain embodiments may cover a sequence of at least about 17, preferably at least about 25, more preferably at least about 50, and most preferably at least about 75 nucleotide residues.

Stringency of conditions employed in hybridizations to establish homology are dependent upon factors such as salt concentration, temperature, the presence of organic solvents, and other parameters. Stringent temperature conditions usually include temperatures in excess of about 30° C., often in excess of about 37° C., typically in excess of about 45° C., preferably in excess of about 55° C., more preferably in excess of about 65° C., and most preferably in excess of about 70° C. Stringent salt conditions will ordinarily be less than about 1000 mM, usually less than about 500 mM, more usually less than about 400 mM, preferably less than about 300 mM, more preferably less than about 200 mM, and most preferably less than about 150 mM. For example, salt concentrations of 100, 50 and 20 mM are used. The combination of the foregoing parameters, however, is more important than the measure of any single parameter. See, e.g., Wetmur et al., *J. Mol. Biol.* 31:349 (1968).

The term "substantially pure" is defined herein to mean a TNF-α convertase or other material that is free from other contaminating proteins, nucleic acids, and other biologicals derived from an original source organism or recombinant DNA expression system. Purity may be assayed by standard methods and will typically exceed at least about 50%, preferably at least about 75%, more preferably at least about 90%, and most preferably at least about 95% purity. Purity evaluation may be made on a mass or molar basis.

Antibody Production

Antigenic (i.e., immunogenic) fragments of the TNF-α convertases of this invention, which may or may not have enzymatic activity, may similarly be produced. Regardless of whether they cleave proTNF-α, such fragments, like the complete TNF-α convertases, are useful as antigens for preparing antibodies, using standard methods, that can bind to the complete enzymes. Shorter fragments can be concatenated or attached to a carrier. Because it is well known in the art that epitopes generally contain at least about five, preferably at least about 8, amino acid residues [Ohno et al., Proc. Natl. Acad. Sci. USA 82:2945 (1985)], fragments used for the production of antibodies will generally be at least that size.

Preferably, they will contain even more residues, as described above. Whether a given fragment is immunogenic can readily be determined by routine experimentation.

Although it is generally not necessary when complete TNF-α convertases are used as antigens to elicit antibody production in an immunologically competent host, smaller antigenic fragments are preferably first rendered more immunogenic by cross-linking or concatenation, or by coupling to an immunogenic carrier molecule (i.e., a macromolecule having the property of independently eliciting an immunological response in a host animal). Cross-linking or conjugation to a carrier molecule may be required because small polypeptide fragments sometimes act as haptens (molecules which are capable of specifically binding to an antibody but incapable of eliciting antibody production, i.e., they are not immunogenic). Conjugation of such fragments to an immunogenic carrier molecule renders them more immunogenic through what is commonly known as the "carrier effect".

Suitable carrier molecules include, e.g., proteins and natural or synthetic polymeric compounds such as polypeptides, polysaccharides, lipopolysaccharides etc. Protein carrier molecules are especially preferred, including but not limited to keyhole limpet hemocyanin and mammalian serum proteins such as human or bovine gammaglobulin, human, bovine or rabbit serum albumin, or methylated or other derivatives of such proteins. Other protein carriers will be apparent to those skilled in the art. Preferably, but not necessarily, the protein carrier will be foreign to the host animal in which antibodies against the fragments are to be elicited.

Covalent coupling to the carrier molecule can be achieved using methods well known in the art, the exact choice of which will be dictated by the nature of the carrier molecule used. When the immunogenic carrier molecule is a protein, the fragments of the invention can be coupled, e.g., using water soluble carbodiimides such as dicyclohexylcarbodiimide or glutaraldehyde.

Coupling agents such as these can also be used to cross-link the fragments to themselves without the use of a separate carrier molecule. Such cross-linking into aggregates can also increase immunogenicity. Immunogenicity can also be increased by the use of known adjuvants, alone or in combination with coupling or aggregation.

Suitable adjuvants for the vaccination of animals include but are not limited to Adjuvant 65 (containing peanut oil, mannide monooleate and aluminum monostearate); Freund's complete or incomplete adjuvant; mineral gels such as aluminum hydroxide, aluminum phosphate and alum; surfactants such as hexadecylamine, octadecylamine, lysolecithin, dimethyldioctadecylammonium bromide, N,N-dioctadecyl-N',N'-bis(2-hydroxymethyl) propanediamine, methoxyhexadecylglycerol and pluronic polyols; polyanions such as pyran, dextran sulfate, poly IC, polyacrylic acid and carbopol; peptides such as muramyl dipeptide, dimethylglycine and tuftsin; and oil emulsions. The polypeptides could also be administered following incorporation into liposomes or other microcarriers.

Information concerning adjuvants and various aspects of immunoassays are disclosed, e.g., in the series by P. Tijssen, Practice and Theory of Enzyme Immunoassays, 3rd Edition, 1987, Elsevier, New York. Other useful references covering methods for preparing polyclonal antisera include Microbiology, 1969, Hoeber Medical Division, Harper and Row; Landsteiner, Specificity of Serological Reactions, 1962, Dover Publications, New York, and Williams, et al., Methods in Immunology and Immunochemistry, Vol. 1, 1967, Academic Press, New York.

Serum produced from animals immunized using standard methods can be used directly, or the IgG fraction can be separated from the serum using standard methods such as plasmaphoresis or adsorption chromatography with IgG-specific adsorbents such as immobilized Protein A. Alternatively, monoclonal antibodies can be prepared.

Hybridomas producing monoclonal antibodies against the TNF-α convertases of the invention or antigenic fragments thereof are produced by well-known techniques. Usually, the process involves the fusion of an immortalizing cell line with a B-lymphocyte that produces the desired antibody. Alternatively, non-fusion techniques for generating immortal antibody-producing cell lines can be used, e.g., virally-induced transformation [Casali et al., Science 234:476 (1986)]. Immortalizing cell lines are usually transformed mammalian cells, particularly myeloma cells of rodent, bovine, and human origin. Most frequently, rat or mouse myeloma cell lines are employed as a matter of convenience and availability.

Techniques for obtaining antibody-producing lymphocytes from mammals injected with antigens are well known. Generally, peripheral blood lymphocytes (PBLs) are used if cells of human origin are employed, or spleen or lymph node cells are used from non-human mammalian sources. A host animal is injected with repeated dosages of the purified antigen (human cells are sensitized in vitro), and the animal is permitted to generate the desired antibody-producing cells before they are harvested for fusion with the immortalizing cell line. Techniques for fusion are also well known in the art, and in general involve mixing the cells with a fusing agent, such as polyethylene glycol.

Hybridomas are selected by standard procedures, such as HAT (hypoxanthine-aminopterin-thymidine) selection. Those secreting the desired antibody are selected using standard immunoassays, such as Western blotting, ELISA (enzyme-linked immunosorbent assay), RIA (radioimmunoassay), or the like. Antibodies are recovered from the medium using standard protein purification techniques [Tijssen, Practice and Theory of Enzyme Immunoassays (Elsevier, Amsterdam, 1985)].

Many references are available to provide guidance in applying the above techniques [Kohler et al., Hybridoma Techniques (Cold Spring Harbor Laboratory, New York, 1980); Tijssen, Practice and Theory of Enzyme Immunoassays (Elsevier, Amsterdam, 1985); Campbell, Monoclonal Antibody Technology (Elsevier, Amsterdam, 1984); Hurrell, Monoclonal Hybridoma Antibodies: Techniques and Applications (CRC Press, Boca Raton, Fla., 1982)]. Monoclonal antibodies can also be produced using well known phage library systems. See, e.g., Huse, et al., Science 246:1275 (1989); Ward, et al., Nature 341:544 (1989).

Antibodies thus produced, whether polyclonal or monoclonal, can be used, e.g., in an immobilized form bound to a solid support by well known methods, to purify the TNF-α convertases by immunoaffinity chromatography.

Antibodies against the antigenic fragments can also be used, unlabeled or labeled by standard methods, as the basis for immunoassays of the TNF-α convertases. The particular label used will depend upon the type of immunoassay. Examples of labels that can be used include but are not limited to radiolabels such as $^{32}P$, $^{125}I$, $^{3}H$ and $^{14}C$; fluorescent labels such as fluorescein and its derivatives, rhodamine and its derivatives, dansyl and umbelliferone; chemiluminescers such as luciferia and 2,3-dihydro-phthalazinediones; and enzymes such as horseradish peroxidase, alkaline phosphatase, lysozyme and glucose-6-phosphate dehydrogenase.

The antibodies can be tagged with such labels by known methods. For example, coupling agents such as aldehydes, carbodiimides, dimaleimide, imidates, succinimides, bisdiazotized benzadine and the like may be used to tag the antibodies with fluorescent, chemiluminescent or enzyme labels. The general methods involved are well known in the art and are described, e.g., in *Immunoassay: A Practical Guide,* 1987, Chan (Ed.), Academic Press, Inc., Orlando, Fla. Such immunoassays could be carried out, for example, on fractions obtained during purification of the TNF-α convertases.

The antibodies of the present invention can also be used to identify particular cDNA clones expressing the TNF-α convertases, in expression cloning systems.

Neutralizing antibodies that bind to the catalytic site of a TNF-α convertase may also be used as inhibitors to block substrate binding, and hence catalytic activity. This can be done using complete antibody molecules, or well known antigen binding fragments such as Fab, Fc, F(ab)$_2$, and Fv fragments.

Definitions of such fragments can be found, e.g., in Klein, *Immunology* (John Wiley, New York, 1982); Parham, Chapter 14, in Weir, ed. *Immunochemistry,* 4th Ed. (Blackwell Scientific Publishers, Oxford, 1986). The use and generation of antibody fragments has also been described, e.g.: Fab fragments [Tijssen, *Practice and Theory of Enzyme Immunoassays* (Elsevier, Amsterdam, 1985)], Fv fragments [Hochman et al., Biochemistry 12:1130 (1973); Sharon et al., Biochemistry 15:1591 (1976); Ehrlich et al., U.S. Pat. No. 4,355,023] and antibody half molecules (Auditore-Hargreaves, U.S. Pat. No. 4,470,925). Methods for making recombinant Fv fragments based on known antibody heavy and light chain variable region sequences have further been described, e.g., by Moore et al. (U.S. Pat. No. 4,642,334) and by Plückthun [*Bio/Technology* 9:545 (1991)]. Alternatively, they can be chemically synthesized by standard methods.

The antibodies and antigen-binding fragments thereof can be used therapeutically to block the activity of a TNF-α convertase, and thereby to treat any medical condition caused or mediated by TNF-α. Such antibodies and fragments are preferably chimeric or humanized, to reduce antigenicity and human anti-mouse antibody (HAMA) reactions. The methodology involved is disclosed, e.g., in U.S. Pat. No. 4,816,397 to Boss et al. and in U.S. Pat. No. 4,816,567 to Cabilly et al. Further refinements on antibody humanization are described in European Patent 451 216 B1.

The dosage regimen involved in a therapeutic application will be determined by the attending physician, considering various factors which may modify the action of the antibodies or binding fragments, e.g., the condition, body weight, sex and diet of the patient, the severity of any infection, time of administration, and other clinical factors.

Typical protocols for the therapeutic administration of antibodies are well known in the art and have been disclosed, e.g., by Elliott et al. [*The Lancet* 344:1125 (1994)], Isaacs et al. [*The Lancet* 340:748 (1992)], Anasetti et al. [*Transplantation* 54:844 (1992)], Anasetti et al. [*Blood* 84:1320 (1994)], Hale et al. [*The Lancet* 2:1394 (Dec. 17, 1988)], Queen [*Scrip* 1881:18 (1993)] and Mathieson et al. [*N. Eng. J. Med.* 323:250 (1990)].

Administration of the compositions of this invention is typically parenteral, by intraperitoneal, intravenous, subcutaneous, or intramuscular injection, or by infusion or by any other acceptable systemic method. Administration by intravenous infusion, typically over a time course of about 1 to 5 hours, is preferred.

Often, treatment dosages are titrated upward from a low level to optimize safety and efficacy. Generally, daily antibody dosages will fall within a range of about 0.01 to 20 mg protein per kilogram of body weight. Typically, the dosage range will be from about 0.1 to 5 mg protein per kilogram of body weight.

Dosages of antigen binding fragments from the antibodies will be adjusted to account for the smaller molecular sizes and possibly decreased half-lives (clearance times) following administration. Various modifications or derivatives of the antibodies or fragments, such as addition of polyethylene glycol chains (PEGylation), may be made to influence their pharmacokinetic and/or pharmacodynamic properties.

It will be appreciated by those skilled in the art, however, that the TNF-α convertase inhibitors of the invention are not limited to neutralizing antibodies or binding fragments thereof. This invention also encompasses other types of inhibitors, including small organic molecules and inhibitory substrate analogs.

One example of a class of small organic molecule inhibitors potentially useful in this invention is a metalloprotease inhibitor designated GI 129471, which has been shown to block TNF-α secretion, both in vitro and in vivo [McGeehan et al., *Nature* 3 70:558 (1994)]. Another such example is N-{D,L-[2-(hydroxyaminocarbonyl)methyl]-4-methylpentanoyl}L-3-(2'naphthyl)-alanyl-L alanine, 2-aminoethyl amide [Mohler et al., *Nature* 370:218 (1994)], which has been shown to protect mice against a lethal dose of endotoxin. Still another example of a small organic molecule inhibitor is a compound, designated SCH 43534, which is mentioned in an example below. This compound is a peptide-based hydroxamate inhibitor of collagenase structurally similar to the foregoing compounds, the inhibitory activity of which validates use of an assay of the invention to identify a TNF-α convertase inhibitor.

The foregoing small organic molecules are not specific inhibitors of a TNF-α convertase but inhibit other metalloproteases as well. As is described more fully below, specific inhibitors of a TNFα convertase which do not inhibit other metalloproteases can also be identified using the methods of this invention if desired.

An "effective amount" of a composition of the invention is an amount that will ameliorate one or more of the well known parameters that characterize medical conditions caused or mediated by TNF-α. Many such parameters and conditions have been described, e.g., as in a review by K. J. Tracey in The Cytokine Handbook, Second Edition, A. Thompson, Ed., 1994, Academic Press Ltd., London, UK, pp. 289–304. The references cited by Tracey are also incorporated herein in their entirety by reference.

Although the compositions of this invention could be administered in simple solution, they are more typically used in combination with other materials such as carriers, preferably pharmaceutical carriers. Useful pharmaceutical carriers can be any compatible, non-toxic substance suitable for delivering the compositions of the invention to a patient. Sterile water, alcohol, fats, waxes, and inert solids may be included in a carrier. Pharmaceutically acceptable adjuvants (buffering agents, dispersing agents) may also be incorporated into the pharmaceutical composition. Generally, compositions useful for parenteral administration of such drugs are well known; e.g. *Remington's Pharmaceutical Science,* 17th Ed. (Mack Publishing Company, Easton, Pa., 1990). Alternatively, compositions of the invention may be introduced into a patient's body by implantable drug delivery systems [Urquhart et al., *Ann. Rev. Pharmacol. Toxicol.* 24:199 (1984)].

Therapeutic formulations may be administered in many conventional dosage formulation. Formulations typically comprise at least one active ingredient, together with one or more pharmaceutically acceptable carriers. Formulations may include those suitable for oral, rectal, nasal, or parenteral (including subcutaneous, intramuscular, intravenous and intradermal) administration.

The formulations may conveniently be presented in unit dosage form and may be prepared by any methods well known in the art of pharmacy. See, e.g., Gilman et al. (eds.) (1990), *The Pharmacological Bases of Therapeutics,* 8th Ed., Pergamon Press; and *Remington's Pharmaceutical Sciences,* supra, Easton, Pa.; Avis et al. (eds.) (1993) *Pharmaceutical Dosage Forms: Parenteral Medications* Dekker, New York; Lieberman et al. (eds.) (1990) *Pharmaceutical Dosage Forms: Tablets* Dekker, New York; and Lieberman et al. (eds.) (1990), *Pharmaceutical Dosage Forms: Disperse Systems* Dekker, New York.

The present invention also encompasses anti-idiotypic antibodies, both polyclonal and monoclonal, which are produced using the above-described antibodies as antigens. These antibodies are useful because they may mimic the structures of the proteases.

Protein Purification

The proteins, polypeptides and antigenic fragments of this invention can be purified by standard methods, including but not limited to salt or alcohol precipitation, preparative disc-gel electrophoresis, isoelectric focusing, high pressure liquid chromatography (HPLC), reversed-phase HPLC, gel filtration, cation and anion exchange and partition chromatography, and countercurrent distribution. Such purification methods are well known in the art and are disclosed, e.g., in *Guide to Protein Purification, Methods in Enzymology,* Vol. 182, M. Deutscher, Ed., 1990, Academic Press, New York, N.Y. More specific methods applicable to purification of the bovine TNF-α convertases are described below.

Purification steps can be followed by carrying out assays for TNF-α convertase activity as described below. Particularly where a convertase is being isolated from a cellular or tissue source, it is preferable to include one or more inhibitors of other proteolytic enzymes is the assay system. Such inhibitors include, e.g., 4-(2-aminoethyl)-benzenesulfonyl fluoride hydrochloride (AEBSF), pepstatin, leupeptin, and methoxysuccinyl-Ala-Ala-Pro-Val-chloromethylketone (AAPV).

Nucleic Acids and Expression Systems

Nucleic acids encoding the TNF-α convertases or fragments thereof can be prepared by standard methods. For example, DNA can be chemically synthesized using, e.g., the phosphoramidite solid support method of Matteucci et al. [*J. Am. Chem. Soc.* 103:3185 (1981)], the method of Yoo et al. [*J. Biol. Chem.* 764:17078 (1989)], or other well known methods. This can be done by sequentially linking a series of oligonucleotide cassettes comprising pairs of synthetic oligonucleotides, as described below.

Of course, due to the degeneracy of the genetic code, many different nucleotide sequences can encode the TNF-α convertases. The codons can be selected for optimal expression in prokaryotic or eukaryotic systems. Such degenerate variants are of course also encompassed by this invention.

Moreover, nucleic acids encoding the TNF-α convertases can readily be modified by nucleotide substitutions, nucleotide deletions, nucleotide insertions, and inversions of nucleotide stretches. Such modifications result in novel DNA sequences which encode antigens having immunogenic or antigenic activity in common with the wild-type enzymes. These modified sequences can be used to produce wild-type or mutant enzymes, or to enhance expression in a recombinant DNA system.

Insertion of the DNAs encoding the TNF-α convertases into a vector is easily accomplished when the termini of both the DNAs and the vector comprise compatible restriction sites. If this cannot be done, it may be necessary to modify the termini of the DNAs and/or vector by digesting back single-stranded DNA overhangs generated by restriction endonuclease cleavage to produce blunt ends, or to achieve the same result by filling in the single-stranded termini with an appropriate DNA polymerase.

Alternatively, desired sites may be produced, e.g., by ligating nucleotide sequences (linkers) onto the termini. Such linkers may comprise specific oligonucleotide sequences that define desired restriction sites. Restriction sites can also be generated by the use of the polymerase chain reaction (PCR). See, e.g., Saiki et al., *Science* 239:487 (1988). The cleaved vector and the DNA fragments may also be modified if required by homopolymeric tailing.

Expression of nucleic acids encoding the TNF-α convertases of this invention can be carried out by conventional methods in either prokaryotic or eukaryotic cells. Although strains of *E. coli* are employed most frequently in prokaryotic systems, many other bacteria such as various strains of *Pseudomonas* and *Bacillus* are know in the art and can be used as well.

Prokaryotic expression control sequences typically used include promoters, including those derived from the β-lactamase and lactose promoter systems [Chang et al., *Nature* 198:1056 (1977)], the tryptophan (trp) promoter system [Goeddel et al., *Nucleic Acids Res.* 8:4057 (1980)], the lambda $P_L$ promoter system [Shimatake et al., *Nature* 292:128 (1981)] and the tac promoter [De Boer et al., *Proc. Natl. Acad. Sci. USA* 292:128 (1983)]. Numerous expression vectors containing such control sequences are known in the art and available commercially.

Eukaryotic expression systems typically insect, mammalian or yeast host cells, for which many expression vectors are known in the art and commercially available.

Screening Systems and Methods

To identify inhibitors of the TNF-α convertases, the enzymes are employed in basic screening systems. Essentially, these systems provide methods for bringing together a mammalian TNF-α convertase, an appropriate substrate for the enzyme, and a sample to be tested for the presence of an inhibitor of the enzyme. If the sample contains such an inhibitor, substantially reduced cleavage of the substrate will be observed, compared to what would be observed in the absence of an inhibitor, e.g., using a "control" sample containing only buffer.

A basic screening method comprises:
(a) contacting a mammalian TNF-α convertase in the presence of substrate with a sample to be tested for the presence of an inhibitor of the convertase; and
(b) measuring the rate of cleavage of the substrate;

whereby an inhibitor of the TNF-α convertase in the sample is identified by measuring substantially reduced cleavage of the substrate, compared to what would be measured in the absence of such inhibitor.

"Substantially reduced cleavage" of a substrate by a TNF-α convertase inhibitor will be observed by measuring less than about 50%, preferably less than about 25%, more preferably less than about 10%, and most preferably less than about 5% of the cleavage measured in the absence of an inhibitor.

The term "sample" is defined herein to mean any solution, whether aqueous, organic of some combination of the two, that may contain a TNF-α convertase inhibitor. Examples of samples include but are not limited to solutions of compounds obtained following organic synthesis, aliquots from purification step fractions, and extracts from cells or tissues, or from other biological or microbial materials.

TNF-α convertase substrates that can be used in the basic assays of the invention include polypeptides comprising the complete proTNF-α sequence, and truncated variants (polypeptides) thereof, the preferred requirement being that all substrates contain the specific Ala-Val bond, the cleavage of which characterizes the TNF-α convertases of the invention. Some examples of such substrates are described below, including a protein (SEQ ID NO: 3) and a polypeptide (SEQ ID NO: 4) substrate. Others are known in the art, such as those disclosed by Mohler et al. [*Nature* 370:218 (1995)]. The term "substrate" is defined herein to mean all such materials. Substrates suitable for use in the assays are preferably based on human proTNF-α, although it may be possible to use substrates from other species.

The substrates can be engineered so that the activity of a TNF-α convertase causes a positive or negative measurable change in the substrate. This may result in a loss or gain of a measurable signal, following cleavage of the substrate.

Any TNF-α convertase can be used in the basic screening methods of this invention, although use of a primate or human enzyme is preferred for the identification of compounds suitable for use as human therapeutics. In connection with the assays, the term "TNF-α convertase" encompasses both the wild-type variants and analogs, such as truncated or substituted variants, as long as they possess substantial proteolytic activity as defined herein. Use of a wild-type, full-length human enzyme is however preferred. Whether a given analog would be suitable for use in an assay of the invention can readily be determined through routine experimentation, using the disclosed methods.

Those skilled in the art will appreciate that there are many ways a mammalian TNF-α convertase could be brought together with a substrate and a test sample to identify an inhibitor, and all such methods are within the scope of this invention. Nevertheless, in a preferred embodiment, a mammalian cell system is employed in which one or more nucleic acids encoding a mammalian TNF-α convertase and a substrate are transfected into a host cell. These nucleic acids can be contained in a single recombinant vector or in two, as is the case in an Example below.

Particularly preferred mammalian host cells for use in the foregoing system inherently lack or have minimal ability to cleave proTNF-α to the mature, secreted form. Examples of such a cell are the 293 human embryonic kidney cell line and clones derived therefrom. The 293 line is available from the American Type Culture Collection, Rockville, Md., under Accession No. ATCC CRL 1573. A clone derived from the 293 line, designated 293EBNA, is available from Invitrogen.

TNF-α convertase inhibitors identified in the basic screens of this invention may be suitable for therapeutic administration, although they may also inhibit other metalloproteases. If it is desired to identify a specific inhibitor of a TNF-α convertase, i.e., one that will not inhibit the activity of other, more general metalloproteases, that can be done using another embodiment of the present invention.

As used herein, the term "specific inhibitor of a TNF-α convertase" is defined to mean an inhibitor which blocks the proteolytic activity of a TNF-α convertase but does not inhibit the activity of collagenase or other matrix-degrading metalloproteases.

The following is a summary of some matrix-degrading metalloproteases, including some names by which they have been called and some of their substrates:

| Enzyme Names | Substrates |
| --- | --- |
| Interstitial Collagenase (MMP-1) | Collagens I, II, III, VII and X |
| 72-kDa Gelatinase (MMP-2) | Collagens IV, V, VII and X |
| Stromelysin (MMP-3) | Collagens III, IV, V and IX |
| Uterine Metalloproteinase (MMP-7) | Gelatins I, III, IV and V |
| Neutrophil Collagenase (MMP-8) | Collagens I, II and III |
| 92-kDa Gelatinase (MMP-9) | Collagens IV and V |
| Stromelysin-2 (MMP-10) | Gelatins I, III, IV and V |

More information on the names and substrates, and on the properties of the above-mentioned matrix-degrading metalloproteases, can be found in a review by Woessner [*FASEB J.* 5:2145 (1991)].

To identify a specific inhibitor of a TNF-α convertase, the screening methods of the invention further comprise:
(a) contacting a matrix-degrading metalloprotease in the presence of substrate with an inhibitor of a TNF-α convertase; and
(b) measuring the rate of cleavage of the substrate;

whereby a specific inhibitor of a TNF-α convertase is identified by measuring substantially undiminished cleavage of the substrate, compared to what would be measured in the absence of such inhibitor.

In a preferred embodiment, a mammalian cell system is employed in which one or more nucleic acids encoding a matrix-degrading metalloprotease and a substrate are transfected into a host cell. These nucleic acids can be contained in a single recombinant vector or in two.

"Substantially undiminished cleavage" of a substrate by a specific inhibitor of a TNF-α convertase will be observed by measuring at least about 75%, preferably at least about 90%, more preferably at least about 95%, and most preferably at least about 99% of the cleavage measured in the absence of such an inhibitor.

Molecular Cloning and Expression

The present invention provides methods for cloning bovine TNFα convertase and corresponding enzymes from other mammalian species. Briefly, Southern and Northern blot analysis can be carried out to identify cells from other species expressing genes encoding the TNF-α convertases. Complementary DNA (cDNA) libraries can be prepared by standard methods from mRNA isolated from such cells, and degenerate probes or PCR primers based on the amino acid sequence information provided herein can be used to identify clones encoding a TNF-α convertase.

Alternatively, expression cloning methodology can be used to identify particular clones encoding a TNF-α convertase. An antibody preparation which exhibits cross-reactivity with TNF-α convertases from a number of mammalian species may be useful in monitoring expression cloning.

Preferably, a co-transfection system described more fully below is used to identify clones capable of cleaving proTNF-α to the mature, secreted form. Selected clones can then be amplified, and cDNA isolated from them can be inserted into vectors suitable for expression in prokaryotic or eukaryotic expression systems.

Briefly, this method for identifying a nucleic acid encoding a mammalian TNF-α convertase comprises:

(a) culturing a mammalian host cell comprising a first recombinant expression vector comprising a nucleic acid encoding a TNF-α convertase substrate and a second recombinant expression vector comprising a nucleic acid that is to be tested to determine whether it encodes a mammalian TNF-α convertase, under conditions in which expression occurs; and (b) measuring the rate of cleavage of the substrate;

whereby a nucleic acid encoding a mammalian TNF-α convertase is identified by measuring substantially increased cleavage of the substrate, compared to what would be measured in the absence of such nucleic acid.

Preferably the TNF-α convertase substrate used is proTNF-α, although any of the other substrates mentioned herein could be used instead.

In the context of this invention, "substantially increased cleavage" of the substrate will be observed by measuring at least about 5 times more, preferably at least about 10 times more, more preferably at least about 25 times more, and most preferably at least about 50 times more cleavage of the substrate than would occur in the absence of a nucleic acid encoding a mammalian TNF-α convertase.

However identified, clones encoding TNF-α convertases from various mammalian species can be isolated and sequenced, and the coding regions can be excised and inserted into an appropriate vector.

Recombinant expression vectors in this invention are typically self-replicating DNA or RNA constructs comprising nucleic acids encoding one of the TNF-α convertases, usually operably linked to suitable genetic control elements that are capable of regulating expression of the nucleic acids in compatible host cells. Genetic control elements may include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also may contain an origin of replication that allows the vector to replicate independently of the host cell.

Vectors that could be used in this invention include microbial plasmids, viruses, bacteriophage, integratable DNA fragments, and other vehicles which may facilitate integration of the nucleic acids into the genome of the host. Plasmids are the most commonly used form of vector but all other forms of vectors which serve an equivalent function and which are, or become, known in the art are suitable for use herein. See, e.g., Pouwels et al., *Cloning Vectors: A Laboratory Manual,* 1985 and Supplements, Elsevier, N.Y., and Rodriguez et al. (eds.), *Vectors: A Survey of Molecular Cloning Vectors and Their Uses,* 1988, Buttersworth, Boston, Mass.

Suitable host cells for expressing nucleic acids encoding the TNF-α convertases include prokaryotes and higher eukaryotes. Prokaryotes include both gram negative and positive organisms, e.g., *E. coli* and *B. subtilis.* Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the TNF-α convertases include but are not limited to those containing the lac promoter (pUC-series); trp promoter (pBR322-trp); lpp promoter (the pIN-series); lambda-pP or pR promoters (pOTS); or hybrid promoters such as ptac (pDR540). See Brosius et al., "Expression Vectors Employing Lambda-, trp-, lac-, and lpp-derived Promoters", in Rodriguez and Denhardt (eds.) *Vectors: A Survey of Molecular Cloning Vectors and Their Uses,* 1988, Buttersworth, Boston, pp. 205–236.

Higher eukaryotic tissue culture cells are preferred hosts for the recombinant production of enzymatically active TNF-α convertases. Although any higher eukaryotic tissue culture cell line might be used, including insect baculovirus expression systems, mammalian cells are preferred. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene.

Suitable expression vectors may be plasmids, viruses, or retroviruses carrying promoters derived, e.g., from such sources as adenovirus, SV40, parvoviruses, vaccinia virus, or cytomegalovirus. Representative examples of suitable expression vectors include pCDNA1, pCD [Okayama et al., *Mol. Cell Biol.* 5:1136 (1985)], pMClneo Poly-A [Thomas et al., *Cell* 51:503 (1987)], pUC19, pREP8, pSVSPORT and derivatives thereof, and baculovirus vectors such as pAC 373 or pAC 610.

EXAMPLES

The present invention can be illustrated by the following examples.

Unless otherwise indicated, percentages given below for solids in solid mixtures, liquids in liquids, and solids in liquids are on a wt/wt, vol/vol and wt/vol basis, respectively. Sterile conditions were generally maintained during cell culture.

General Methods

Standard methods were used, as described, e.g., in Maniatis et al., *Molecular Cloning: A Laboratory Manual,* 1982, Cold Spring Harbor Laboratory, Cold Spring Harbor Press; Sambrook et al., *Molecular Cloning: A Laboratory Manual,* (2d ed.), Vols 1–3, 1989, Cold Spring Harbor Press, NY; Ausubel et al., *Biology,* Greene Publishing Associates, Brooklyn, N.Y.; or Ausubel, et al. (1987 and Supplements), *Current Protocols in Molecular Biology*, Greene/Wiley, New York; Innis et al. (eds.) *PCR Protocols: A Guide to Methods and Applications*, 1990, Academic Press, N.Y.

In vitro Assays for TNF-α Convertase Activity

For the assay of convertase activity associated with or isolated from membrane preparations, a protein-based assay was carried out essentially as described by Mohler et al., *Nature* 370:218 (1995).

Briefly, a peptide-tagged recombinant human TNF-α protein substrate (Flag-TNF-α) was cloned and expressed in *E. coli*. The protein was purified by affinity chromatography using an M2 (anti-Flag)-Sepharose column (Kodak), and by ion exchange chromatography using a BIOCAD equipped with an HQ10 column.

The amino acid sequence of the protein substrate is defined in the Sequence Listing by SEQ ID NO: 3, concerning which the following should be noted. Amino acid residues 2–9 comprise the "Flag" sequence. Residues 10 and 11 are a Gly-Ser connector following the Flag which were added to accommodate a restriction site used in construction. The histidine at position 12 corresponds to the histidine at position −25 of SEQ ID NO: 1, after which the two sequences are identical to the carboxyl termini. Thus, fifty residues of the normal leader sequence of human proTNF-α have been deleted from this substrate. Since the deleted region is not essential for use as a substrate in an assay of this invention, other truncations containing deletion of more or fewer residues could be used as well.

To test for convertase activity, a membrane protein sample (12 μg) was mixed (in 12 μl) with 2 ng of $^{125}$I-polypeptide substrate (approximately 50,000 cpm) in the presence of inhibitors of other proteolytic enzymes [e.g., 200 μM 4-(2-aminoethyl)-benzenesulfonyl fluoride hydrochloride (AEBSF), 2 μM pepstatin, 200 μM leupeptin, 1 mM methoxysuccinyl-Ala-Ala-Pro-Val-chloromethylketone (AAPV)], and with or without 2.5 mM EDTA. Following incubation at 37° C. overnight, samples were fractionated in a 16% sodium dodecylsulfate (SDS) gel and subjected to SDS polyacrylamide gel electrophoresis [SDS-PAGE; Laemmli, *Nature* 227:680 (1970)]. The gels were dried, and radioactivity was detected by autoradiography.

Examination of the gels revealed intensified bands from the samples incubated without EDTA, at the position expected for the 17 kDa human TNF-α cleavage product.

A polypeptide-based assay for TNF-α convertase activity was also carried out essentially using the method of Mohler et al., supra. Briefly, an amino-terminal dinitrophenylated peptide substrate, amidated at the carboxyl terminus (SEQ ID NO: 4) was synthesized and purified using standard procedures. Dinitrophenylated polypeptides corresponding to cleavage products expected for TNF-α convertase (a dinitrophenylated peptide having the sequence of residues 1–6 of SEQ ID NO: 4) and for other membrane proteases were also synthesized.

To test for convertase activity, a membrane protein sample was mixed in 50 μl with 1 μg peptide substrate in the presence of inhibitors (0.2 mM AEBSF, 2 μM pepstatin, 200 μM leupeptin, 1 mM AAPV). Following incubation at 37° C. for from 60 minutes to overnight, the protein was precipitated by cold 5% trichloroacetic acid (TCA), 20% acetonitrile, and the soluble peptide fraction was applied to a YMC 120 angstrom C-18 ODS-AQ column (4.6×100 mm; YMC, Inc.). The column was eluted isocratically at a flow rate of 1 ml/min using 40% acetonitrile plus 0.06% trifloroacetic acid. The elution of DNP-peptide was monitored at 360 nm using a Waters 625 LC system.

The results of a typical assay are shown in FIG. 1, wherein the positions of the uncut peptide and an expected convertase cleavage product (DNP-APLAQA) are shown. Of course, other cleavage products attributable to the activities of other proteases present in the crude membrane sample were also observed; some of their elution positions are also shown in FIG. 1.

Preparation and Sequencing of Bovine TNF-α Convertases

Bovine spleen purchased from Pel-Freeze was cut into small pieces, washed in cold PBS, and then shredded using a Black & Decker POWER PRO food processor. The tissue was resuspended in lysis buffer [20 mM Tricine (N-[2-Hydroxy-1,1-bis(hydroxymethyl)-ethyl] glycine), pH 7.8, 8% sucrose] containing 0.1% PMSF, then homogenized using a Brinkmann POLYTRON tissue homogenizer. Cell debris was removed by two centrifugations at 8,000×g, and the membranes were isolated by ultracentrifugation at 60,000×g. The isolated membranes were washed in 10 mM Hepes, pH 7.5, then resuspended and frozen at −20° C. until used.

The membrane fraction was thawed and resuspended to a concentration of 8 mg/ml protein in Buffer A (20 mM Tris, pH 7.5, 1 mM $MgSO_4$, 10 mM NaCl, 10 μM $ZnSO_4$) plus 2% Brij 35 (23 lauryl ether), and incubated at 4° C. for 30 minutes. The membranes were collected by ultracentrifugation at 60,000×g, then resuspended to 4 mg/ml in buffer A plus 2% Lubrol (polyethylene glycol monododecyl ether). The insoluble protein was removed by ultracentrifugation at 60,000×g.

The Brij-insoluble, lubrol-solubilized membrane protein fraction was adjusted to 0.3 M NaCl and applied to a chelating Sepharose column charged with nickel sulfate. The column was washed and eluted with wash buffer (Buffer A with 0.3 M NaCl and 0.1% octyl glucoside) plus 50 mM imidazole. The eluate was concentrated by ultrafiltration, then applied to a S300 sieving column equilibrated in buffer A plus 0.1% octylglucoside. A retained fraction (corresponding to a molecular weight of approximately 60,000) was pooled, adjusted to 0.3 M NaCl and applied to a wheat germ agglutinin column.

The retained fraction was eluted with 0.5 M N-acetyl glucosamine in Buffer A with 0.5 M NaCl, dialyzed against 1 mM sodium phosphate buffer, pH 7, and applied to a hydroxyapatite column. The unbound fraction was passed over an HQ-10 ion exchange column (Perseptive Biosystems), and eluted with a linear gradient of from 0 to 500 mM NaCl. Fractions containing TNF-α convertase activity were pooled for further characterization.

The final protein fraction (approximately 10 μg) of the first bovine TNF-α convertase was applied to an 8% polyacrylamide gel in SDS-glycine buffer (Novex). Following electrophoresis, the gel was stained for 8 minutes in 10% acetic acid/50% methanol containing 0.1% Coomassie blue, then destained for 3.5 hours in three changes of 10% acetic acid/50% methanol. The polypeptide was excised and subjected to in situ tryptic cleavage, peptide isolation and microsequencing using standard methods.

This enzyme was a bovine TNF-α convertase, amino acid sequences of which are disclosed above.

The purification of bovine ADAM 10 was carried out by subjecting bovine spleen to the procedures described above to the point of application to the wheat germ agglutinin column. Thereafter, the retained fraction was eluted with 0.5 M N-acetyl glucosamine, dialyzed against 1 mM sodium phosphate buffer, pH 7, and applied to an hydroxyapatite column. A bound fraction from that column was passed over an HQ-10 ion exchange column.

The unbound fraction, containing the TNF-α convertase activity (approximately 10 μg) was subjected to electrophoresis an 8% polyacrylamide gel using SDS-glycine buffer (Novex) with dithiothreitol. Following electrophoresis, the fractionated proteins were electophoretically transferred to an IMMOBILON filter membrane in 10 mM CAPS (3-[Cyclohexylamino]-1-propanesulfonic acid) buffer, pH 10, with 10% methanol. The protein band was visualized by staining the membrane 0.1% Ponceau S in 40% methanol, 10% acetic acid, excised, and subjected to in situ tryptic cleavage, peptide isolation and microsequencing, including N-terminal analysis, using standard methods.

Cloning of Human MT-MMP1, MT-MMP2, MT-MMP3, MMP7, MMP12 and Bovine ADAM 10

Human MT-MMP1 cDNA was cloned from THP-1 cell (ATCC TIB 202) total RNA, which was converted to single-stranded DNA using a GibcoBRL SUPERSCRIPT Preamplification System (Catalog #18089-011) and an oligo dT primer. This DNA was then 35 used directly for PCR using primers designated #5261 (SEQ ID NO: 5; 5' forward primer) and #5271 (SEQ ID NO: 6; 3' reverse primer). PCR conditions were: 94° C., 30 seconds/60° C., 30 seconds/72° C., 2 minutes, for 30 cycles. The PCR product was cut with KpnI/HindIII and ligated into similarly cut pSVSPORT (GibcoBRL).

Cloning of human MT-MMP2 was initiated by isolating total RNA from THP-1 cells and preparing single-stranded DNA as described above. The DNA was then subjected to a two-step PCR protocol to obtain the full-length MT-MMP2 cDNA as follows.

First, two PCR reactions were run that encompassed overlapping front and back halves of MT-MMP2. One reaction was set up using primers designated #B5295GD (SEQ ID NO: 7; 5' forward) and "reverse internal" (SEQ ID NO: 8; internal 3'). A second PCR reaction was set up using primers #B5296GD (SEQ ID NO: 9; 3' reverse) and "forward internal" (SEQ ID NO: 10; internal 5'). PCR conditions were as described above. The product of each of these reactions was isolated by agarose gel electrophoresis.

In the second step, the two products from the PCR reactions were mixed with PCR primers B5295GD and B5296GD, and PCR was performed under the same conditions as described above. The product from this reaction was cut with EcoRI/XbaI, isolated by agarose gel electrophoresis, and cloned into vector pSRαSPORT that had been cut with the same restriction enzymes.

Human MT-MMP3 was cloned as described for MT-MMP1 but from aorta polyA+ RNA (Clontech) using PCR primers designated #5322 (SEQ ID NO: 11; 5' forward primer) and #5323 (SEQ ID NO: 12; 3' reverse primer). The PCR product was cut with KpnI/HindIII, isolated, and cloned into vector pSRαSPORT that had been cut with the same restriction enzymes.

Similarly, human MMP7 (matrilysin) was cloned from human testis poly A+ RNA (Clontech) and using PCR primers #5367 (SEQ ID NO: 13; 5' forward primer) and #5369 (SEQ ID NO: 14; 3' reverse primer). The PCR product was cut with KpnI/HindIII, isolated, and cloned into vector pSRαSPORT that had been cut with the same restriction enzymes.

Human MMP12 (macrophage metalloelastase) was similarly cloned from human aorta polyA+ RNA using PCR primers #A0698H03 (SEQ ID NO: 15; 5' forward primer) and #A0698H08 (SEQ ID NO: 16; 3' reverse primer). The PCR product was cut with KpnI/XbaI and, following isolation, cloned into similarly-cut vector pSRαSPORT.

Bovine ADAM 10 was cloned as described above from 5 μg of total RNA isolated from bovine spleen poly A+ RNA (Clontech). The resulting single-stranded DNA was then used for PCR, using primers having sequences defined in the Sequence listing by SEQ ID NO: 17 (5' forward primer) and SEQ ID NO: 18 (3' reverse primer). PCR conditions were as described above, and the PCR product was digested with KpnI and HindIII and ligated into similarly-digested vector pCEP4 (Invitrogen).

Construction of a Human proTNF-α Expression Vector

Human proTNF-α cDNA can be cloned from total RNA isolated from LPS (lipopolysaccharide)-stimulated THP-1 cells and converted to single-stranded DNA as described above. This DNA can then be used for PCR, e.g., using primers designed to introduce BamHI cleavage sites into the PCR product. The sequences of suitable 5'0 and 3' primers are defined in the Sequence Listing by SEQ ID NO: 19 and SEQ ID NO: 20, respectively. The PCR product is then cut with BamHI to produce an insert that can be cloned into a BamHI-cleaved expression vector.

A similar insert was ligated into pUC 19 (New England Biolabs) that had been cut with Bam HI, to produce a vector designated pUCTNF. Vector pUCTNF was then cut with SalI/HindIII, and a fragment retaining the coding region for proTNF-α was ligated into a vector designated pSRαSPORT that had cut with the same restriction enzymes. Vector pSRαSPORT had previously been constructed as follows.

pSVSPORT 1 (GibcoBRL) was cut with ClaI/PstI to remove the SV promoter and treated with Klenow polymerase to fill in the ClaI overhang and produce a blunt end. A fragment containing the SRα promoter and SV40 t antigen was obtained following cleavage of plasmid pDSRG (ATCC 68233; International Patent Application Publication No. WO 91/01078) with HindIII/PstI and filling of the HindIII overhang with Klenow polymerase. This fragment was then ligated into the cut pSVSPORT 1 to produce pSRαSPORT.

Cloning of a Novel Human Protein

Vector pSRαSPORT was cleaved using NotI/SalI, and a 1.5 kb stuffer cDNA fragment was ligated into the cut vector. The stuffer cDNA fragment, which was a neomycin resistance gene, was prepared by digesting plasmid PMClneo Poly A (Stratagene, Catalog No. 213201) with XhoI/SalI, and the small fragment was isolated and ligated into SalI-digested pSL1190 (Pharmacia, catalog No. 27–4386). The stuffer fragment was released by digesting the resulting vector pSC1190-Neo with SalI, and the 1.5 kb fragment was isolated.

The construct incorporating the stuffer fragment was cleaved using NotI/SalI, and the linearized vector was separated from the insert cDNA by agarose gel electrophoresis. The cleaved vector was then repurified in a second agarose electrophoresis gel. The pure cleaved vector DNA was isolated from the agarose gel using GELZYME (Invitrogen), following the recommended conditions. This vector was used to clone library cDNA.

Messenger RNA was prepared by treating Mono Mac-6 cells [Ziegler-Heitbrock et al., *Int. J. Cancer* 41:456 (1988)] with lipopolysaccharide at 1 μg/ml for 18 hours, and with PMA at 10 ng/ml for one hour prior to RNA isolation. Total RNA was prepared from these cells using the guanidine thiocyanate method (Sambrook et al., supra, pp. 7.19–7.22). The cells were collected by centrifugation, resuspended in guanidine thiocyanate (Gibco BRL) with 2.5 grams of N-laurylsarcosine sodium salt (Sigma), 5 drops of anti-foam A (Sigma) and 0.75 ml of 2-mercaptoethanol (Biorad).

The lysate was layered over an equal volume of 5.7 M cesium chloride solution and centrifuged in an SW41 rotor for 24 hours at 25,000 rpm. The resulting total RNA pellet was washed with ethanol, resuspended in sterile water, and treated with DNAse by incubating 500 µg of total RNA per ml in buffer containing 5 units of RQ1 DNAse I (Promega), 400 units of RNAsin (Promega), 10 mM $MgCl_2$, and 5 mM DTT at 37° C. for 30 min. The solution was treated with an equal volume of 1:1 phenol/chloroform solution, and the RNA was precipitated with ethanol. $PolyA^+$ mRNA was isolated from the total RNA using the OLIGOTEX mRNA isolation system (Qiagen Inc.).

Five micrograms of mRNA were used to synthesize cDNA following the protocols in the SUPERSCRIPT Plasmid System for cDNA synthesis and plasmid cloning (Gibco BRL), with the following modifications. Following second strand synthesis, the cDNA was phenol/chloroform extracted, ethanol precipitated, and then treated with T4 DNA Polymerase (Pharmacia LKB), following the manufacturer's instructions. Following NotI digestion, the resuspended cDNA was subjected to electrophoresis in 1% SEA-PLAQUE GTG agarose (FMC) and visualized by ethidium bromide staining. The portion of the gel from 2 kb to 13 kb was excised and digested with GELZYME (Invitrogen).

The resulting size-enriched cDNA was ligated with the NotI/SalI-cleaved pSRαSport vector overnight using a 2:1 vector/insert concentration ratio. The ligation mixture was then extracted with phenol/chloroform, precipitated with ethanol, and electroporated into ELECTROMAX DH10B cells (Gibco BRL) under the prescribed conditions. The cells were plated out at a density of about 1000 colonies per plate, with a total of around $7 \times 10^5$ colonies for the entire library.

Cells from each plate were collected in 1.5 ml Luria broth. An aliquot (500 µl) of each pool was mixed with 250 µl of 80% (v/v) glycerol, and stored at −20° C. The remaining cells were collected by centrifugation, and plasmid DNA isolated using the QIAWELL 8 Ultra Plasmid Kit (Qiagen) following the recommended procedures. Final DNA preparation was eluted from the Qiawell resin with two 100 µl aliquots of 10 mM Tris pH8.

Positives from an initial 800 plasmid pools were identified using the cell transfection assay described below and then split into pools of 50 colonies per plate, and DNA was prepared as described above. Positives from secondary assays were then spread onto Petri plates, and 144 individual colonies were picked. DNA was prepared from each clone as described above, and all positive pools were reconfirmed in duplicate by retransfection and ELISA at each step before proceeding.

Plasmid DNA was sequenced by the Taq DyeDeoxy™ Terminator Cycle Sequencing kit and method (Perkin-Elmer/Applied Biosystems) in two directions using an Applied Biosystems Model 373A DNA Sequencer. Sequence alignment was performed using ABI SEQED Analysis and Sequence Navigator software. The results are shown in SEQ ID NO: 21, which provides the complete open reading frame nucleotide sequence together with the predicted amino acid sequence.

When co-transfected into 293EBNA cells with the vector encoding human proTNF-α as described below, the novel cDNA caused the production of soluble, mature TNF-α. This activity was inhibited by SCH 43534.

Cell Transfection TNF-α Convertase Assay System

To develop an effective cell-based assay system, it was first necessary to identify host cells that substantially lacked TNF-α convertase activity. This was accomplished by transiently transfecting a number of cell types with an expression vector encoding a substrate such as human proTNF-α, and then assaying for the expected cleavage products, as is explained more fully below.

It thus was established that although COS cells possess significant TNF-α convertase activity, the human embryonic kidney cell line 293 and a clone derived therefrom, designated 293EBNA, lacked the ability to cleave transfected human proTNF-α. That was true even though all of the cells when transfected with a vector expressing a human growth hormone as a control secreted that product. For that reason, 293/293EBNA cells are preferred transfection hosts for the assay described below.

This assay system was established using nucleic acids encoding known membrane-type matrix metalloproteases, some of which possess TNF-α convertase activity as defined herein. Using this system in conjunction with a vector(s) encoding one of the specific human membrane-type matrix metalloproteases or bovine ADAM 10, and human proTNF-α, specific TNF-α convertase inhibitors can be identified.

Moreover, the same system can also be used to identify other nucleic acids encoding other mammalian TNF-α convertases as well. That can be accomplished by substituting nucleic acids from cDNA or other libraries for the nucleic acids encoding the exemplary matrix metalloproteases, and observing TNF-α convertase activity expressed thereby.

To demonstrate use of this basic assay system, host cells were transfected in one of two ways. In one method, human 293EBNA cells (Invitrogen) at $5 \times 10^6/0.25$ ml of RPMI with 10% fetal bovine serum (FBS) were placed in a 0.4 cm electroporation-cuvette with 5 µg total DNA. The cells were electroporated using a GENE PULSER (BioRad) at 200V, 960 µFd, and 100 ohms. After recovering for 5 minutes, the cells were diluted into 15 ml of medium and placed in a tissue culture flask at 37° C., 5% $CO_2$.

In a second method, transfections were carried out using Lipofectin (GibcoBRL). DNA (2 µg total) was mixed with 10 µl of Lipofectin in 200 µl of serum free medium (Opti-MEM, GibcoBRL) at room temperature for 15 minutes. Then 600 µl of Opti-MEM was added and the mixture added to $10^6$ 293EBNA cells. After 4 hours at 37° C., 200 µl of 50% FBS were added, and the supernatant was collected 24–48 hours later for analysis. For smaller numbers of cells the conditions were scaled down proportionally.

The Lipofectin method was also used to assay for bovine ADAM 10 activity, whereby 1 µl of Lipofectin was diluted into 10 µl of OPTI-MEM medium and allowed to stand at room temperature for 30 minutes. The solution was mixed with 10 µl of OPTI-MEM containing 50 ng of proTNFα-SRαSPORT with or without 100 ng of ADAM 10-pCEP4, and allowed to stand at room temperature for 15 minutes. Sixty µl of OPTI-MEM were added, and the entire 80 µl were used to replace the spent growth medium in the seeded wells. After incubation at 37° C., 5% $CO_2$ for 5 hours, 20 µl of DME containing 50% fetal bovine serum were added to the well. Following incubation at 37° C., 5% $CO_2$ for 20 hours, the medium was assayed for TNFα production.

To detect convertase activity, enzyme-linked immunosorbant assay (ELISA) was carried out by diluting a human TNF-α capture antibody (Pharmingen #18631D) to 1 µg/ml in 0.1 M $NaHCO_3$, pH 8.2, and coating the solution onto a 96 well Nunc MAXISORP microtiter plate at 100 µl/well overnight at 4° C. The wells were then blocked with 200

µl/well of PBS containing 10% FBS and 0.1% azide and stored at 4° C. until used for assay.

Immediately prior to use, the microtiter wells were washed with PBS containing 0.05% Tween 20 (polyoxyethylenesorbitan monolaurate). Samples and standards were diluted in PBS containing 10% FBS, added at 100 µl/well, and incubated at 37° C. for 2 hours. After washing as described above, 100 µl of biotinylated anti-TNF-α (Pharmingen #18642D) were added at 1 µg/ml in PBS with 10% FBS and incubated for 45 minutes at 22° C. After washing twice with PBS and Tween 20, streptavidin-HRP (BioSource) was added at a 1:50 dilution, 100 µl/well in PBS with 10% FBS, and incubated for 30 minutes at 22° C. After washing three times with PBS and Tween 20, ABTS substrate (KP Labs) was added at 100 µl/well, and color development was stopped at an appropriate time determined by visual inspection by addition of 100 µl/well of 1% SDS. The plates were read at 405 nm using a Molecular Devices microtiter plate reader.

Cleavage of proTNF-α by Human MT-MMP1, MT-MMP2 and MT-MMP3 and by Bovine ADAM 10

Figure 2:
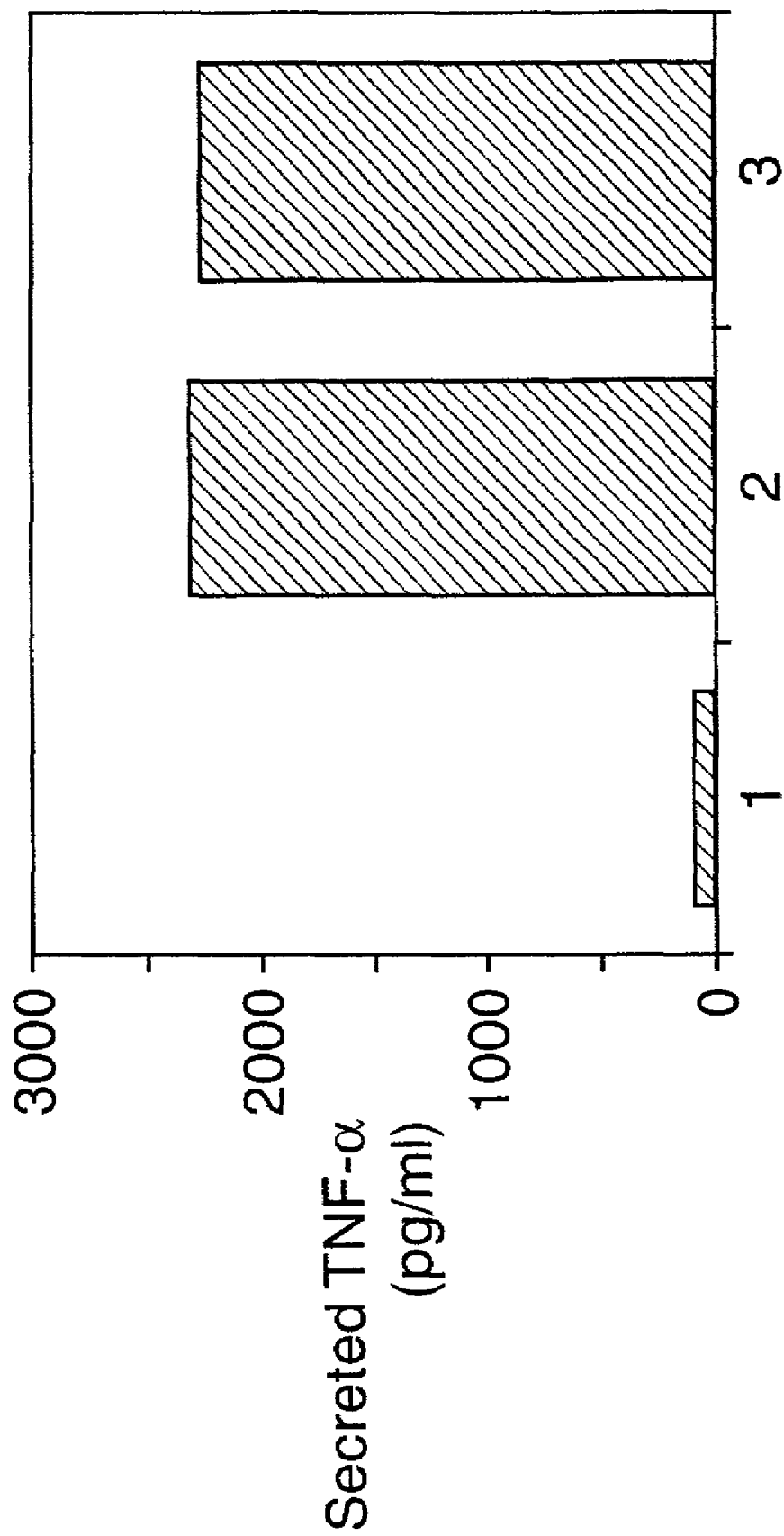
FIG. 2 is a graphical representation of results from an assay in which human proTNF-α was cleaved by membrane-type matrix metalloproteases MT-MMP1 and MT-MMP3.

DNA encoding MT-MMP1 or MT-MMP3 described above was cloned into expression vector pREP8 (Invitrogen) and co-transfected with the vector encoding human proTNF-α into 293EBNA cells. Following an assay carried out as described above, it was observed that both of the matrix metalloproteases caused cleavage of the proTNF-α. This is evident in FIG. 2, where the results produced using proTNF-α alone (Bar 1), proTNF-α plus MT-MMP1 (Bar 2), and proTNF-α plus MT-MMP3 (Bar 3) are shown. Similar activity was not shown by MMP7 or by MMP12.

It was further found that as little as 6 pg/transfection of MT-MMP1 produced a clear secreted TNF-α signal by ELISA. This was determined by varying the amount of MT-MMP1 vector in the presence of a constant amount of proTNF-α (50 ng/transfection) and empty pREP8 vector (100 ng/transfection). Thus, this system is useful for identifying other TNF-α convertases by expression cloning.

Although the data are not shown, similar results were obtained for MT-MMP2

Similar results were also obtained using bovine ADAM 10.

TNF-α Convertase Inhibitor Assay

To demonstrate use of the transfection assay system to detect inhibitors of a human TNF-α convertase, 293EBNA cells were co-transfected with expression vectors encoding human proTNF-α and MT-MMP1 as described above, and assayed in the presence or absence of varying amounts of an MMP inhibitor, designated SCH 43534, which had previously been shown to block the release of TNF-α from activated human THP-1 cells.

Figure 3:
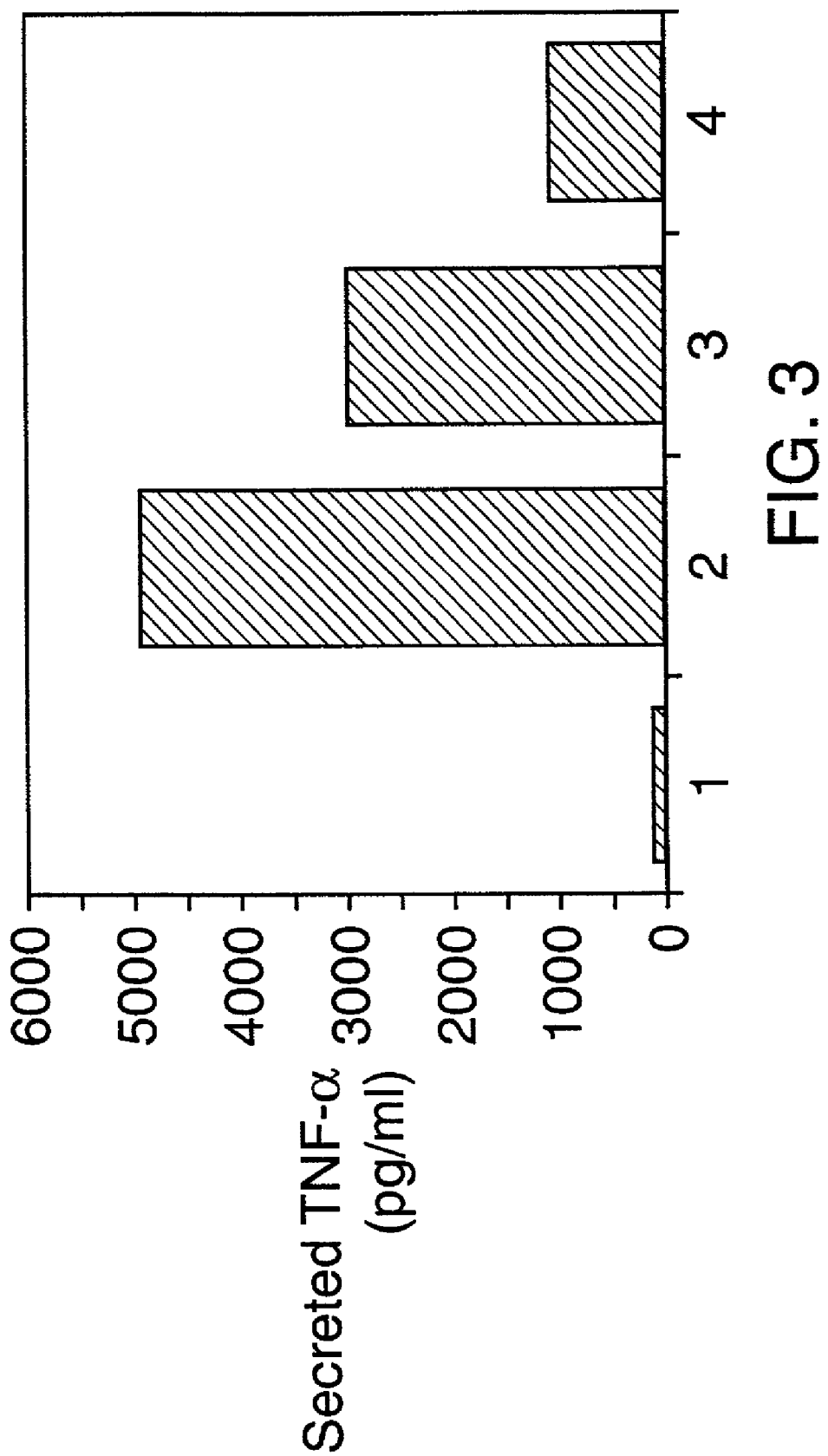
FIG. 3 is a graphical representation of results from an assay in which cleavage of human proTNF-α by MT-MMP1 was inhibited by varying amounts of an MMP inhibitor.

The results are shown in FIG. 3 for proTNF-α alone (Bar 1), proTNF-α plus MT-MMP1 (Bar 2), proTNF-α plus MT-MMP1 plus 1 µM SCH 43534 (Bar 3), and proTNF-α plus MT-MMP1 plus 10 µM SCH 43534 (Bar 4).

Similar results were obtained using bovine ADAM 10. It thus is clear that the present assay can be used to detect inhibitors of TNF-α convertase activity as defined herein.

Many modifications and variations of this invention can be made without departing from its spirit and scope, as will be apparent to those skilled in the art. The specific embodiments described herein are offered by way of example only, and the invention is to be limited only by the terms of the appended claims, together with the full scope of equivalents to which such claims are entitled.

What is claimed is:

1. An isolated antibody or antigen binding fragment thereof which specifically binds to the TNF-α convertase having the amino acid sequence set forth in SEQ ID NO:23.

2. The antibody of claim 1, wherein said antibody is a monoclonal antibody.

3. The antibody of claim 1, wherein said antibody is a polyclonal antibody.

4. The antibody of claim 1, wherein said antibody is a neutralizing antibody.

5. The antibody of any one of claims 2–4, wherein said antibody is labeled.

6. The antibody of claim 1, wherein said antibody is PEGylated.

7. The antigen binding fragment of claim 1, wherein said fragment is selected from the group consisting of F(ab)₂, Fab and Fv.

8. The antibody or antigen binding fragment thereof of claim 1, wherein said antibody or fragment is bound to a solid support.

9. The antibody or antigen binding fragment thereof of claim 1, wherein said antibody or fragment is conjugated to a carrier.

10. A pharmaceutical composition comprising the antibody or antigen binding fragment thereof of claim 1, and a pharmaceutically acceptable carrier.

* * * * *